United States Patent [19]

Rusin et al.

[11] Patent Number: 5,814,682
[45] Date of Patent: Sep. 29, 1998

[54] METHOD OF LUTING A PROVISIONAL PROSTHETIC DEVICE USING A GLASS IONOMER CEMENT SYSTEM AND KIT THEREFOR

[76] Inventors: Richard P. Rusin; Paula D. Ario; Dwight W. Jacobs; Joel D. Oxman; Sumita B. Mitra; Ronald M. Randklev, all of P.O. Box 33427, St. Paul, Minn. 55133-3427

[21] Appl. No.: 663,727

[22] Filed: Jun. 14, 1996

[51] Int. Cl.$^6$ .................................................. C08K 3/34
[52] U.S. Cl. ...................... 523/116; 523/118; 433/228.1; 524/556; 524/832; 524/433
[58] Field of Search .................... 524/556, 832, 524/443; 523/116, 118; 433/228.1

[56] References Cited

U.S. PATENT DOCUMENTS

| | | | |
|---|---|---|---|
| 3,655,605 | 4/1972 | Smith et al. | 260/29.6 M |
| 3,814,717 | 6/1974 | Wilson et al. | 260/29.6 M |
| 4,016,124 | 4/1977 | Crisp et al. | 260/29.6 M |
| 4,053,321 | 10/1977 | Okumiya et al. | 106/57 |
| 4,089,830 | 5/1978 | Tezuka et al. | 260/29.6 H |
| 4,143,018 | 3/1979 | Crisp et al. | 260/29.6 M |
| 4,209,434 | 6/1980 | Wilson et al. | 260/29.6 H |
| 4,342,677 | 8/1982 | Muramatsu et al. | 523/116 |
| 4,360,605 | 11/1982 | Schmitt et al. | 523/116 |
| 4,376,835 | 3/1983 | Schmitt et al. | 523/116 |
| 4,503,169 | 3/1985 | Randklev | 523/117 |
| 4,695,251 | 9/1987 | Randklev | 433/8 |
| 5,063,257 | 11/1991 | Akahane et al. | 523/116 |
| 5,084,491 | 1/1992 | Kerby | 523/116 |
| 5,130,347 | 7/1992 | Mitra | 522/149 |
| 5,154,762 | 10/1992 | Mitra et al. | 106/35 |
| 5,215,459 | 6/1993 | Ney et al. | 433/215 |
| 5,332,429 | 7/1994 | Mitra et al. | 106/35 |

FOREIGN PATENT DOCUMENTS

| | | |
|---|---|---|
| 3413864 | 1/1985 | Germany . |
| C-3413864 | 1/1985 | Germany . |
| WO-A-9103987 | 4/1991 | WIPO . |
| WO-A-9522956 | 8/1995 | WIPO . |

OTHER PUBLICATIONS

Crisp et al., "Characterization of glass–ionomer cements", Journal of Dentistry, 5 No. 1, 1977, pp. 51–56.

Wilson et al., "Characterization of glass–ionomer cements", Journal of Dentistry, N, No. 2, 1977, pp. 117–120.

Wilson et al., "Experimental Luting Agents Based on the Glass Inomer Cements", Brit. Dent. Journal, 142, 1977, pp. 117–122.

Wilson et al., "Glass–Ionomer Cement", Chapter 6, 1988 by Quintessence Publishing Co., Inc., Chicago, IL, pp. 83–85.

Wilson, "Developments in Glass–Ionomer Cements", International Journal of Prosthodontics, vol. 2, No. 5, 1989, pp. 438–446.

McCaghren, et al., "Shear Bond Strength of Light–cured Glass Ionomer to Enamel and Dentin", Journal Dent. Res., vol. 69, No. 1, 1990, pp. 40–45.

Christensen, "Glass ionomer as a luting material", JADA, vol. 120, Jan. 1990, pp. 59–62.

Morgan et al., "Solving Endodontic Isolation Problems with Interim Buildups of Reinforced Glass Ionomer Cement", Journal of Endodontics, vol. 16, No. 9, Sep. 1990, pp. 450–453.

Billington et al., "Variation in powder/liquid ratio of a restorative glass–ionomer cement used in dental practice", British Dental Journal, 169, Sep. 1990 pp. 164–167.

Breeding et al., "Use of luting agents with an implant system: Part I", Journal of Prosthetic Dentistry, Nov. 68, No. 5, Nov. 1992, pp. 737–741.

Liebenberg, "Wire–reinforced, light–cured glass ionomer–resin provisional restoration: A description of the technical procedure", Journal of Prosthetic Dentistry, vol. 72, No. 3, Sep. 1994, pp. 337–341.

Lieve Van Zeghbroeck, "Glass Ionomers: The Next Generation", 2nd International Symposium on Glass Ionomers, Philadelphia, PA Jun. 1994, pp. 227–228.

Dentsply Brochure, "Advance Hybrid Ionomer Cement", No. 574005 (Oct. 1994).

Vivadent Brochure, "Provilink", No. V543458/295/5/e/VbgL (no date available).

*Primary Examiner*—Andrew E. C. Merriam
*Attorney, Agent, or Firm*—Dale A. Bjorkman

[57] ABSTRACT

The present invention provides a method of luting a provisional prosthetic device to tooth structure using glass ionomer cement systems having reduced bulk shear adhesion. The invention also provides a kit for luting a prosthetic device to tooth structure. The kit contains at least three containers of glass ionomer luting cement compositions. The kit advantageously can be utilized for providing both a provisional and a permanent luting cement depending upon which components are admixed.

12 Claims, No Drawings

METHOD OF LUTING A PROVISIONAL PROSTHETIC DEVICE USING A GLASS IONOMER CEMENT SYSTEM AND KIT THEREFOR

FIELD OF THE INVENTION

This invention relates to glass ionomer cement systems. More specifically, this invention relates to a method of luting a provisional prosthetic device using glass ionomer cement systems having reduced bulk shear adhesion.

BACKGROUND OF THE INVENTION

Glass ionomer cements in general are materials that comprise an ionic polymer component and a reactive glass component, where mixing these two components in an aqueous environment initiates a cement setting reaction. These materials are used in a number of applications in the dental and medical industries where a cement is used on, for example, tooth or bone structure. Glass ionomers, in general, have traditionally been considered to provide good adhesion to tooth structure. In order to provide materials with wide applicability, considerable effort has been expended in increasing the strength and adhesion of conventional glass ionomer systems.

Glass ionomer cements have been disclosed for use as a wide variety of permanent dental materials and as temporary materials for certain specific dental applications.

U.S. Pat. No. 5,084,491 to Kerby discloses dental filling materials comprising stainless steel filler, a polymeric binder, and glass filler. These cements are disclosed as having utility as 1) a core build up filling material prior to crown preparation; 2) core-filling material in combination with a prefabricated post to restore route-canal treated teeth; 3) temporary or permanent filling material of primary or permanent teeth or dental implants; and 4) a luting agent for the cementation of permanent dental restorations (see Column 3, Lines 34–43).

A. D. Wilson and J. W. McLean, *Glass-Ionomer Cement*, Quintessence Publishing Co., Inc., 1988, Chicago, Ill., Chapter 6 entitled "Adhesion", pp. 83–85 discuss tensile and shear bond strength of glass ionomers to dentin and enamel. Although some of the commercial materials reported had low bond strengths, there is no suggestion to use these materials as provisional luting agents.

L. C. Breeding, D. L. Dixon, M. T. Bogacki and J. D. Tietge, "Use of Luting Agents with an Implant System: Part I", *The Journal of Prosthetic Dentistry*, Vol. 68, No. 5, 1992, pp. 737–741 report the use of a glass ionomer cement as a permanent luting agent to cement implant abutments to implant fixtures. Three temporary cements, none of which are glass ionomer, are independently used to provisionally bond cast crowns to implant abutments and natural tooth abutments.

Lieve Van Zeghbroeck, "Cements: Clinical Use of Glass Ionomer Luting Cements" in *Glass Ionomers: The Next Generation* (Edited by Peter R. Hunt), Proceedings of the 2nd International Symposium on Glass Ionomers, Philadelphia, Pa., June 1994, Published by International Symposium in Dentistry, PC, Philadelphia, Pa., p. 228 discusses the need for a cement which retains the restoration for a distinct period of time, but which still allows "command" removal of the restoration. However, this reference provides no teaching as to how such a material could be formulated or the physical properties it theoretically should exhibit.

SUMMARY OF THE INVENTION

The present invention provides a method of luting a provisional prosthetic device to tooth structure comprising the steps of:

(a) applying to at least a portion of the prosthetic device or tooth structure a glass ionomer cement comprising:
  (i) water-miscible, acidic polymer;
  (ii) finely-divided, acid-reactive filler; and
  (iii) a sufficient amount of an adhesion reducing component such that the cement has a Bulk Shear Adhesion less than 2.0 MPa;
    (b) placing and adhering the provisional device to the tooth structure;
    (c) removing the provisional device; and
    (d) cementing a permanent prosthetic device to the tooth structure.

The present invention also provides a kit for luting a prosthetic device to tooth structure comprising:

(a) water miscible, acidic polymer;
(b) a first formulation of a finely divided, acid-reactive filler; and
(c) a second formulation of a finely divided, acid-reactive filler, wherein a provisional luting cement formed by admixing (a) and (b) has a Bulk Shear Adhesion less than 2.0 MPa and a permanent luting cement formed by admixing (a) and (c) has a Bulk Shear Adhesion greater than 2.0 MPa.

Another kit configuration comprises:

(a) a first formulation of a water miscible, acidic polymer;
(b) a second formulation of a water miscible, acidic polymer; and
(c) finely divided, acid-reactive filler, wherein a provisional luting cement formed by admixing (a) and (c) has a Bulk Shear Adhesion less than 2.0 MPa and a permanent luting cement formed by admixing (a) and (b) has a Bulk Shear Adhesion greater than 2.0 MPa.

DETAILED DESCRIPTION

Applicants have discovered a method of luting provisional prosthetic devices to tooth structure using glass ionomer cement formulations as described herein that exhibit bulk shear adhesion properties that enable the cement to advantageously be used as a low adhesion luting cement. Specifically, the glass ionomer luting cement systems exhibit Bulk Shear Adhesion less than 2.0 MPa, preferably less than 1.0 MPa and more preferably less than 0.5 MPa. These luting cements are particularly useful for use as luting agents for cementation of provisional prosthetic devices. By "provisional" is meant a device that is a short term substitute for a device that is intended to replace all or part of tooth structure for an indefinite period of time. These provisional (i.e., temporary) devices may be in place for as short a time period as a few days to as long as a year or more. Typically, they are in the mouth for a period of one to three weeks.

The term "luting cement", as used herein, refers to a composition that is used to anchor or hold a prosthetic device in place in the mouth. The luting cement is the composition that is used to adhere the prosthesis, i.e., a crown, bridge, inlay, onlay or veneer, to the tooth. This is in contrast to use of a similar composition as a tooth filling material which comprises the major tooth replacement portion of the restoration.

Provisional prosthetic devices generally are either custom-made forms that conform closely to the prepared tooth or prefabricated shells that are adjusted chairside to fit onto the prepared tooth. The composition of these provisional devices includes, but is not limited to, metal, such as tin-silver alloy or anodized aluminum, polycarbonate, acrylic, conventional provisional crown and bridge materials or conventional dental resins. The devices may be unlined or lined with acrylic or resin material. Generally with the custom-made forms only a provisional cement is used to bond them to the tooth. Prefabricated shells, on the other hand, generally are lined to fill the often substantial space between the shell and the tooth. The liner provides strength to prevent wear-through and good marginal adaptation. The prefabricated shells may be lined with an acrylic or resin material prior to cementation in place with the provisional luting cement of the invention or may be filled with the provisional luting cement and then placed on the tooth structure. In the latter instance, the provisional cement serves as both the liner and the cement.

The low adhesion glass ionomer luting cement system as set forth above allows for easy clean up of excess cement expressed from the prosthetic device when the device is seated with a water spray. It also allows for easy removal of the provisional prosthetic device when the practitioner deems it appropriate to replace it with a permanent device. The beneficial fluoride releasing properties of a glass ionomer cement provide anticaries protection in the interim period during which the provisional prosthesis is in place. Other benefits of a fluoride releasing provisional luting cement include non-irritation and desensitization of the dentin.

In addition to low bulk shear adhesion, strength is important for a glass ionomer provisional luting cement because the luting cement serves as the foundation for an overlying prosthetic device. Strength may be measured as compressive strength ("CS") and as diametral tensile strength ("DTS"). Compared to commercially available temporary cements, the luting cement system of the invention exhibits both higher CS and higher DTS as well as compatibility with all provisional prosthetic devices and all conventional permanent luting cements. High strength is particularly important in instances where an unlined prosthesis is utilized.

The provisional luting cements of the invention may be provided in single or multi-part formulations. For example, they may be provided as two-part formulations such as powder:liquid, paste:paste and paste:liquid. However, the formulations may be provided in more than two parts, if desired. Conventionally, these types of materials have been sold as two-part systems, wherein the ionic polymer is provided in an aqueous liquid form and the reactive glass is provided as a powder.

The provisional luting cement of the invention may advantageously be provided as a kit in a number of configurations. Kits having three or more containers of glass ionomer luting cement compositions may be provided. The kit may include, for example, two powder formulations for admixture with a single liquid or two liquid formulations for admixture with a single powder. For the former, the practitioner could mix the liquid with one of the powders to obtain a low adhesion luting cement for use with a provisional prosthetic device and after removal of the provisional prosthetic device, by mixing the same liquid with the other powder, a high adhesion luting cement for use with a permanent prosthetic device could be provided. Also both the first and the second formulations could be provided as powders for admixture with water.

Another useful kit configuration may include a first container of a powder, a second container of a liquid and a third container of adhesion reducing component(s). In this instance, the practitioner would admix the powder, the liquid and the adhesion reducing component to form the provisional luting cement. After removal of the provisional prosthetic device, the powder and liquid would be admixed to provide the permanent luting cement. Thus, with a single kit, the practitioner could be able to make up either a provisional or a permanant luting cement depending upon which components were admixed. Any kit configuration that provides both a provisional and permanent luting cement with admixture of certain of the kit components, provides not only a simplified system, but also a system wherein the provisional and permanent cement are compatible. Useful kit configurations other than those mentioned above will be apparent to those skilled in the art.

In order to avoid confusion and enable the practitioner to easily distinguish the components of a kit configured as mentioned above, a colorant (i.e., a pigment or dye) could be incorporated into one or more of the kit components. Such colorant may exhibit, for example, a color change upon setting or with a change in pH in order to provide a more aesthetic luting cement.

The term "ionomer", as used herein, refers to a polymer having sufficient pendent ionic groups to undergo a setting reaction in the presence of a reactive filler and water. It also includes a composition containing a monomer, polymer or oligomer or mixtures thereof with sufficient pendent polymerizable groups to enable the resulting mixture to be polymerized via a non-ionic setting reaction, e.g., cured via a redox reaction or upon exposure to radiant energy.

The term "water miscible", as used herein, refers to a polymer that dissolves at least partially in water or in water combined with (an)other ingredient(s). The other ingredient (s) may include, for example, a cosolvent and/or surfactant. The term "water soluble", as used herein, refers to a polymer that dissolves in water alone.

The term "reactive filler", as used herein, refers to a metal oxide or hydroxide, mineral silicate, or ion-leachable glass that is capable of reacting with the ionomer in the presence of water to form a hydrogel.

The term "non-reactive filler", as used herein, refers to filler materials that do not react with the ionomer in the presence of water to form a hydrogel.

The term "ionomer cement system", as used herein, refers to the unmixed, or mixed but unset and uncured, combination of ionomer, reactive filler, and other optional ingredients, such as water.

The term "working time", as used herein, refers to the time between the beginning of the setting reaction, i.e., when the ionomer and reactive filler are combined in the presence of water, and the time the setting reaction has proceeded to the point at which it is no longer practical to perform further physical work upon the system, e.g., spatulate it or reform it, for its intended dental or medical purpose.

The term "setting time", as used herein, refers to the time between the beginning of the setting reaction in a cement, and the time sufficient hardening has occurred to allow subsequent clinical procedures to be performed. Such hardening can occur by the ionic setting reaction and/or by a non-ionic setting reaction.

Suitable water miscible acidic polymers include, but are not limited to, homo- or copolymers of unsaturated mono-, di- and tricarboxylic acids, particularly homo- or copolymers of acrylic acid, itaconic acid and maleic acid.

Preferred ionomers of the present invention comprise a polymer having sufficient pendent ionic groups to undergo a setting reaction in the presence of a reactive filler and water, and sufficient pendent non-ionically polymerizable groups to enable the resulting mixture to be cured by a redox curing mechanism and/or by exposure to radiant energy.

Preferred ionomers have the general Formula I:

$$B(X)_m(Y)_n \qquad I$$

wherein

B represents an organic backbone, each X independently is an ionic group capable of undergoing a setting reaction in the presence of water and a reactive filler, each Y independently is a non-ionically polymerizable group, m is a number having an average value of 2 or more, and n is a number having an average value of 1 or more.

Preferably the backbone B is an oligomeric or polymeric backbone of carbon-carbon bonds, optionally containing non-interfering substituents such as oxygen, nitrogen or sulfur heteroatoms. The term "non-interfering" as used herein refers to substituents or linking groups that do not unduly interfere with either the ionic or the non-ionic polymerization reaction.

Preferred X groups are acidic groups, with carboxyl groups being particularly preferred.

Suitable Y groups include, but are not limited to, polymerizable ethylenically unsaturated groups and polymerizable epoxy groups. Ethylenically unsaturated groups are preferred, especially those that can be polymerized by means of a free radical or redox mechanism, examples of which are substituted and unsubstituted acrylates, methacrylates, alkenes and acrylamides. In aqueous systems, polymerizable groups that are polymerized by a cationic mechanism, e.g., polymerizable ethylenically unsaturated groups such as vinyl ether groups and polymerizable epoxy groups, are less preferred since a free radical mechanism is typically easier to employ in such systems than a cationic mechanism.

X and Y groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups.

Ionomers of Formula I can be prepared according to a variety of synthetic routes, including, but not limited to, (1) reacting n X groups of a polymer of the formula $B(X)_{m+n}$ with a suitable compound in order to form n pendent Y groups, (2) reacting a polymer of the formula $B(X)_m$ at positions other than the X groups with a suitable compound in order to form n pendent Y groups, (3) reacting a polymer of the formula $B(Y)_{m+n}$ or $B(Y)_n$, either through Y groups or at other positions, with a suitable compound in order to form m pendent X groups and (4) copolymerizing appropriate monomers, e.g., a monomer containing one or more pendent X groups and a monomer containing one or more pendent Y groups.

The first synthetic route referred to above is preferred, i.e., the reaction of n X groups of a polymer of the formula $B(X)_{m+n}$ to form n pendent Y groups. Such groups can be reacted by the use of a "coupling compound", i.e., a compound containing both a Y group and a reactive group capable of reacting with the polymer through an X group in order to form a covalent bond between the coupling compound and the X group, thereby linking the Y group to the backbone B in a pendent fashion. Suitable coupling compounds are organic compounds, optionally containing non-interfering substituents and/or non-interfering linking groups between the Y group and the reactive group.

Particularly preferred ionomers of Formula I are those in which each X is a carboxyl group and each Y is an ethylenically unsaturated group that can be polymerized by a free radical or redox mechanism. Such ionomers are conveniently prepared by reacting a polyalkenoic acid (e.g., a polymer of formula $B(X)_{m+n}$ wherein each X is a carboxyl group) with a coupling compound containing both an ethylenically unsaturated group and a group capable of reacting with a carboxylic acid group. The molecular weight of the resultant ionomers is preferably between about 250 and about 500,000, and more preferably between about 1,000 and about 100,000. As referred to herein, "molecular weight" means weight average molecular weight. These ionomers are generally water-soluble, but to a lesser extent than the polyalkenoic acids from which they are derived. Hence, the use of cosolvents, as described more fully below, is preferred in order to enhance the solubility of the ionomers and achieve more concentrated solutions thereof.

Suitable polyalkenoic acids for use in preparing ionomers of this invention include those homopolymers and copolymers of unsaturated mono-, di-, or tricarboxylic acids commonly used to prepare glass ionomer cements. Representative polyalkenoic acids are described, for example, in U.S. Pat. Nos. 3,655,605, 4,016,124, 4,089,830, 4,143,018, 4,342,677, 4,360,605 and 4,376,835.

Preferred polyalkenoic acids are those prepared by the homopolymerization and copolymerization of unsaturated aliphatic carboxylic acids, for example acrylic acid, 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid and tiglic acid. Suitable monomers that can be copolymerized with the unsaturated aliphatic carboxylic acids include unsaturated aliphatic compounds such as acrylamide, acrylonitrile, vinyl chloride, allyl chloride, vinyl acetate, and 2-hydroxyethyl methacrylate ("HEMA"). Ter- and higher polymers may be used if desired. Particularly preferred are the homopolymers and copolymers of acrylic acid. The polyalkenoic acid should be surgically acceptable, that is, it should be substantially free from unpolymerized monomers and other undesirable components.

Particularly preferred polyalkenoic acids also include homopolymers of polyacrylic acid, and copolymers of acrylic and itaconic acids, acrylic and maleic acids, methyl vinyl ether and maleic anhydride or maleic acid, ethylene and maleic anhydride or maleic acid, and styrene and maleic anhydride or maleic acid.

Polymers of formula $B(X)_{m+n}$ can be prepared by copolymerizing an appropriate mixture of monomers and/or comonomers. Preferably, such polymers are prepared by free radical polymerization, e.g., in solution, in an emulsion, or interfacially. Such polymers can be reacted with coupling compounds in the presence of appropriate catalysts.

Coupling compounds suitable for use for preparing the preferred ionomers of the present invention include compounds that contain at least one group capable of reacting with X in order to form a covalent bond, as well as at least one polymerizable ethylenically unsaturated group. When X is carboxyl, a number of groups are capable of reacting with X, including both electrophilic and nucleophilic groups. Examples of such groups include the following moieties, and groups containing these moieties: —OH, —NH$_2$, —NCO, —COCl, and

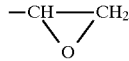

Examples of suitable coupling compounds include, but are not limited to, acryloyl chloride, methacryloyl chloride, vinyl azalactone, allyl isocyanate, HEMA, 2-aminoethylmethacrylate, and 2-isocyanatoethyl methacrylate. Other examples of suitable coupling compounds include those described in U.S. Pat. No. 4,035,321, the disclosure of which is hereby incorporated by reference. Examples of preferred coupling compounds include, but are not limited to, the following methacrylate compounds and their corresponding acrylates.

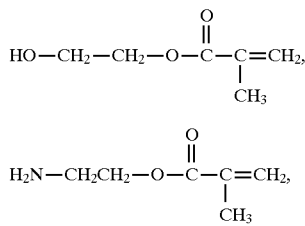

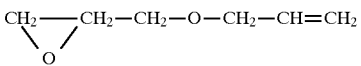

Particularly preferred coupling compounds are the following methacrylate compounds and their corresponding acrylates, wherein R is as defined above.

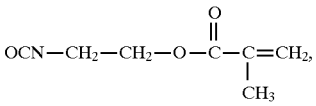

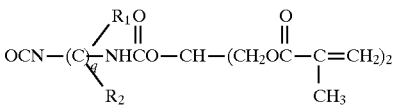

wherein q is 1 to 18 and $R^1$ and $R^2$ are as defined above.

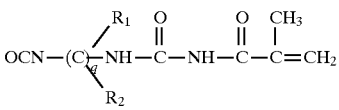

wherein q is as defined above,

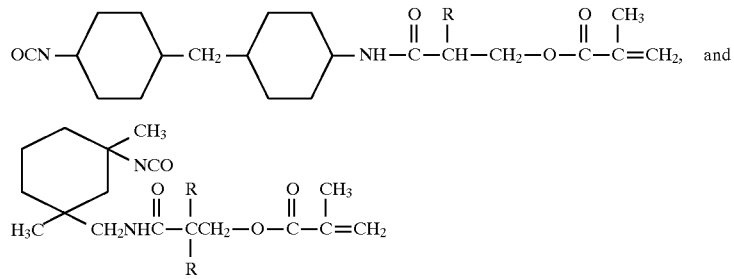

-continued

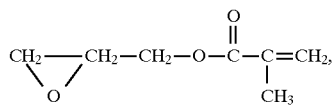

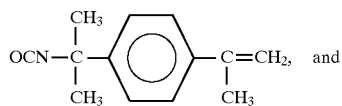

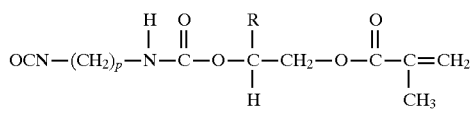

wherein p is 1 to 20 and R, $R^1$ and $R^2$ are H or lower alkyl (e.g., having 1 to 6 carbon atoms), as well as the following allyl and vinyl compounds.

Preferred ionomers of Formula I are prepared by reacting a polymer of formula $B(X)_{m+n}$ wherein X is COOH with a coupling compound containing a reactive group of the formula NCO. The resultant ionomers, e.g., those of Formula I above wherein the covalent bond between the X group and the reactive group of the coupling compound is an amide linkage. These ionomers provide an optimal combination of such properties as adhesion to dentin, mechanical strength, working time, fluoride release and the like.

Reactive fillers suitable for use in the cement systems of this invention include those that are commonly used with ionomers to form ionomer cements. Examples of suitable reactive fillers include metal oxides such as zinc oxide and magnesium oxide, and ion-leachable glasses, e.g., as described in U.S. Pat. Nos. 3,655,605, 3,814,717, 4,143,018, 4,209,434, 4,360,605 and 4,376,835.

The reactive filler is preferably a finely divided reactive filler. The filler should be sufficiently finely divided so that it can be conveniently mixed with the other ingredients and provide a film thickness in accordance with ISO Standard 3107 of less than about 25 micrometers for use as a luting cement. Preferred average particle diameters for the filler are about 0.2 to about 15 micrometers, more preferably about 1 to 10 micrometers, as measured using, for example, a sedimentation analyzer. In general, use of a reactive filler having larger average particle size will provide a luting cement with lower adhesion.

Preferred reactive fillers are acid-reactive. Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fluoroaluminosilicate glasses are particularly preferred. Suitable reactive fillers are also available from a variety of commercial sources familiar to those skilled in the art. For example, suitable fillers can be obtained from a number of commercially available glass ionomer cements, such as "GC Fuji LC" cement and "Kerr XR" ionomer cement. Mixtures of fillers can be used if desired.

If desired, the reactive filler can be subjected to a surface treatment. Suitable surface treatments include acid washing, treatment with phosphates, treatment with chelating agents such as tartaric acid, treatment with a silane or silanol coupling agent. Particularly preferred reactive fillers are silanol treated fluoroaluminosilicate glass fillers, as described in U.S. Pat. No. 5 5,332,429, the disclosure of which is expressly incorporated by reference herein.

The amount of reactive filler should be sufficient to provide a cement having desirable mixing and handling properties before cure and good cement performance after cure. Preferably, the reactive filler represents less than about 90%, more preferably about 25% to about 85%, and most preferably about 50% to about 80% by weight of the total weight (including water) of the unset cement components.

Non-reactive fillers may be selected from one or more of any material suitable for incorporation in compositions used for medical applications, such as fillers currently used in dental restorative compositions and the like. The filler is finely divided and has a maximum particle diameter less than about 15 micrometers in order to provide a luting cement with a film thickness in accordance with ISO Standard 3107 of less than about 25 micrometers. The filler preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable non-reactive inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.); metallic powders such as those disclosed in U.S. Pat. No. 5,084,491, especially those disclosed at column 2, lines 52–65. Examples of suitable non-reactive organic filler particles include filled or unfilled pulverized polycarbonates, polyepoxides, and the like. Preferred non-reactive filler particles are quartz, submicron silica, and non-vitreous microparticles of the type described in U.S. Pat. No. 4,503,169. Mixtures of these non-reactive fillers are also contemplated, as well as combination fillers made from organic and inorganic materials.

Preferably the surface of the non-reactive filler particles is treated with a coupling agent in order to enhance the bond between the filler and the polymerizable resin. The use of suitable coupling agents include gamma-methacryloxypropyltrimethoysilane, gamma-mercaptopropyltriethoxysilane, gamma-aminopropyltrimethoxysilane, and the like.

The low bulk shear adhesion ionomer cement systems of the invention also contain one or more adhesion reducing components. An adhesion reducing component may be any of a number of components that are present in sufficient quantity to provide a provisional luting cement with a Bulk Shear Adhesion less than 2.0 MPa. Adhesion reducing components include, but are not limited to, salts or bases to partially neutralize the polyalkenoic acid, non-acid reactive species to reduce the proportion of acid-reactive species in the cement system and substitution of some or all of the polyalkenoic acid with a polyalkenoic acid of lower molecular weight. The adhesion reducing component may be added to one or more of the multi-part formulations of the cement and may be added in such amount as to provide a set luting cement having a Bulk Shear Adhesion in the range desired for its intended purpose. Mixtures of the aforementioned adhesion reducing components may be utilized.

Suitable salts or bases that can be used to partially neutralize the polyalkenoic acid of the cement system generally include salts or bases wherein the pKa of the conjugate acid of the salt is greater than the pKa of the polyalkenoic acid. Preferred salts and bases are sodium citrate, potassium phosphate, monoammonium phosphate, sodium hydroxide, potassium hydroxide, lithium, sodium or potassium salts, magnesium oxide, sodium oleate, hydrated or non-hydrated sodium phosphates and hydrated or non-hydrated potassium phosphates. Typically, the salt or base will be present in about 0.001 to about 10 weight %, preferably from about 0.5 to about 5 weight %, based on the total weight of the cement composition.

Suitable non-acid reactive species include any or all of the non-reactive fillers mentioned above, either alone or in combination. Suitable non-acid reactive species also include chelating agents such as tartaric acid. For incorporation into a paste or liquid formulation, suitable non-acid reactive species additionally include water, glycerol, polyethylene glycol, polypropylene glycol, polyvinyl acetate and non-acid reactive monomers, polymers and oligomers, e.g., polyethylene glycol dimethacrylate, glycerol dimethacrylate, bisphenol A diglycidyl methacrylate ("Bis-GMA"), triethylene glycol dimethacrylate ("TEGDMA"), HEMA, polypropylene glycol dimethacrylate, urethane dimethacrylate and any other resin suitable for incorporation into conventional dental materials. Preferred non-acid reactive species are zirconia:silica microparticles, submicron silica, water, glycerol, polyethylene glycol dimethacrylate, TEGDMA and HEMA. Typically, the non-acid reactive species will be present in about 1 to about 95 weight %, preferably from about 10 to about 80 weight %, based on the total weight of the cement composition.

Substitution of some or all of the polyalkenoic acid with a polyalkenoic acid of lower molecular weight may be utilized to provide a provisional luting cement with low bulk shear adhesion. For example, a polyacid, e.g., polyacrylic acid, with a molecular weight of 2,000 may be used instead of a polyacid having a molecular weight of 25,000 to 40,000. Preferred commercially available polyacids include those sold by Aldrich Chemical Co., Inc. with molecular weights of 2,000, 5,000, 90,000 and 250,000 and polyacrylic acid sold under the tradename "GOODRITE" (from BFGoodrich Co., Specialty Polymers & Chemicals Division, Cleveland, Ohio) and available in molecular weights ranging from 2,000 to 240,000. The lower molecular weight polyacids generally have a lower solids content. When desiring to formulate a paste incorporating these lower molecular weight polyacids, the polyacids can be concentrated without undesirable gellation to achieve a solids content equivalent to or higher than a commercially available higher molecular weight polyacid. Typically, the polyalkenoic acid of lower molecular weight will be present in about 2 to about 40 weight %, preferably from about 3 to about 20 weight %, based on the total weight of the cement composition.

The low bulk shear adhesion luting cement of the invention may be used with or without a primer. A primer may be applied to the tooth structure prior to adhering the provisional prosthesis to reduce or enhance the adhesion of the luting cement to the tooth structure. For example, an adhesion reducing primer may be applied to tooth structure prior to placement of a provisional prosthetic device with the provisional luting cement of the invention in instances in which the provisional luting cement has a Bulk Shear Adhesion in the range of 1 to 2 MPa or in instances in which the practitioner intends the prosthetic device to remain in place only a few days. On the other hand, an adhesion enhancing primer may to applied to tooth structure prior to placement of a provisional prosthetic device with the provisional luting cement of the invention in instances in which the luting cement has a Bulk Shear Adhesion less than about 0.5 MPa or in instances in which the practitioner intends the prosthetic device to remain in place for a period longer than the typical one to three weeks.

Suitable adhesion reducing primers include, but are not limited to, petrolatum, glycerol, polyethylene glycol, polyvinyl acetate, silicones, oils, surfactants either alone or dissolved or suspended in a suitable solvent, colloidal silica, colloidal alumina, a slurry of fine particles of any of the non-reactive fillers mentioned above and a solution of any of the salts or bases mentioned above. Preferred adhesion reducing primers are petrolatum, glycerol, a slurry of fine particles of zirconia:silica microparticles, alumina or titania, and a solution of salts or bases mentioned above, e.g., sodium phosphate in water.

Suitable adhesion enhancing primers include, acidic solutions. More preferably, the adhesion enhancing primers are acidic solutions also containing a hydrophilic resin. More preferably, the adhesion enhancing primer is an acidic solution comprising a hydrophilic resin and components having ethylenic unsaturation. Most preferably, the adhesion enhancing primer comprises a compound having both acidic functionality and ethylenic unsaturation. Examples of commercially available primers include the primers sold as components of the 3M™ Scotchbond™ Multi-Purpose Dental Adhesive System (3M) and 3M™ Vitremer™ Core Build-Up/Restorative Glass Ionomer System (3M).

In addition to the ionic setting reaction, the ionomer cement system may also incorporate other modes of initiation of the crosslinking reaction. A preferred additional mode for initiation of the crosslinking reaction is the incorporation of an oxidizing agent and a reducing agent as a redox catalyst system to enable the dental composition to cure via a redox reaction. Various redox systems and their use in ionomer cements is described in U.S. Pat. No. 5,154,762, the disclosure of which is expressly incorporated herein by reference. A metal complexed ascorbic acid is a preferred reducing agent that provides cure with excellent color stability. This system is more fully described in U.S. patent application Ser. No. 08/202,931, the disclosure of which is expressly incorporated herein by reference.

The oxidizing agent should react with or otherwise cooperate with the reducing agent to produce free radicals capable of initiating polymerization of the ethylenically unsaturated moiety.

The preferred amount for each of the reducing agent and the oxidizing agent is about 0.01 to about 10%, more preferably about 0.02 to about 5%, based on the total weight (including water) of the unset cement components.

The oxidizing agent and the reducing agent preferably are sufficiently shelf stable and free of undesirable coloration to permit their storage and use under typical dental conditions. The oxidizing agent and the reducing agent should also preferably be sufficiently soluble and present in an amount sufficient to permit an adequate free radical reaction rate. This can be evaluated by combining all of the ingredients of the cement except for the filler under safelight conditions and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include ascorbic acid, metal complexed ascorbic acid, cobalt (II) chloride, ferrous chloride, ferrous sulfate, hydrazine, hydroxylamine, oxalic acid, thiourea and salts of a dithionite, thiosulfate, benzene sulfinate, or sulfite anion.

Metal complexed ascorbic acid is a particularly preferred reducing agent. The metal complexed ascorbic acid provides a dental composition that exhibits color stability and maintains the catalytic potency of the ascorbic acid. Any metallic ion that can form stable complexes with ascorbic acid can be used. Preferred metals include the transition metals and metals of group IA, IIA, and IIIB. Particularly preferred complexing metals are zirconium and aluminum with aluminum being most preferred. The desired metal complexed ascorbic acid is preferably prepared using a suitable metal alkoxide or metal salt.

The ionomer cement systems of the invention may optionally contain one or more suitable initiators that act as a source of free radicals when activated by heat or light. Such initiators can be used alone or in combination with one or more accelerators and/or sensitizers.

The initiator should be capable of promoting free radical crosslinking of the ethylenically unsaturated moiety on exposure to light of a suitable wavelength and intensity. It also preferably is sufficiently shelf stable and free of undesirable coloration to permit its storage and use under typical dental conditions. Visible light photoinitiators are preferred. The photoinitiator preferably is water soluble or water miscible. Photoinitiators bearing polar groups usually have a sufficient degree of water solubility or water miscibility. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium, triarylsulfonium and aryldiazonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator, when utilized, should be present in an amount sufficient to provide the desired rate of polymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

Optional other ingredients, such as modifying agents, cosolvents and stabilizers can be added at any time and in any manner that does not prematurely begin the ionic or non-ionic setting reaction.

Modifying agents can be used in the ionomer cement systems of the present invention in order to provide prolonged working times. Modifying agents useful in the cement system of the present invention are, for example, alkanolamines, e.g., ethanolamine and triethanolamine, and mono-, di- and tri-sodium hydrogenphosphates. The modifying agents are preferably used at about 0.1 to about 10 weight %, and preferably between about 0.5 to about 5 weight %, based on the weight of the reactive filler.

Cosolvents useful in the present invention include, but are not limited to, low molecular weight organic solvents. The word "cosolvent", as used herein refers to a material that aids in the dissolution of an ionomer in water, in order to form a homogeneous aqueous solution of cosolvent and ionomer. Suitable cosolvents include non-copolymerizable organic solvents and copolymerizable low molecular weight hydrophilic alkenyl solvents. The word "copolymerizable" as used herein refers to the ability of the cosolvent to cure compatibly with the ionomers used in the invention. Copolymerizable cosolvents can be added to the ionomer cement systems of this invention for a variety of reasons, for instance, to provide a homogeneous solution of a photocurable ionomer having inherently low aqueous solubility, to shorten the exposure of radiant energy needed to cure the system, or to vary the physical properties, e.g., the flexibility, of the resultant cured ionomer cement. Examples of suitable cosolvents include non-copolymerizable cosolvents such as ethanol, propanol, and glycerol, and copolymerizable cosolvents such as HEMA or 2-hydroxypropylmethacrylate.

Stabilizers may be incorporated into the compositions of the invention and are particularly desirable for paste formulations. Oxalic acid and sodium metabisulfite are preferred stabilizers.

If desired, the cements of the invention can contain adjuvants such as pigments, inhibitors, accelerators, viscosity modifiers, medicaments, fluoride sources and other ingredients that will be apparent to those skilled in the art.

The components of the glass ionomer cement system can be combined, e.g., blended or mixed, in a variety of manners and amounts in order to form the low adhesion luting cement of this invention. Suitable combining techniques include those commonly employed to mix ionomer cement systems. Mixture by spatulation is preferred for a powder:liquid or paste:liquid system, but a paste:paste system lends itself well to delivery using a multiple barrel syringe delivery system using a static mixing element to assure adequate mixing of the two pastes. Such a system is described in pending U.S. patent application Ser. Nos. 08/202,390 and 08/394,724, the disclosures of which are expressly incorporated by reference herein.

Sufficient amounts of each component in the cement systems of the present invention should be employed to obtain the desired working time. Preferably such systems will provide a working time of at least about one minute and more preferably greater than two minutes, during which time the systems can be cured by exposure to an appropriate source of radiant energy. For the sake of brevity this discussion will focus on dental applications, and particularly, the curing of such systems in situ, e.g., in the mouth of a patient.

The curing of the ionomer cement system may be optionally accomplished by exposure to any source of radiant energy capable of causing the desired extent of polymerization of the photocurable ionomer. Suitable radiant energy sources afford a desired combination of such properties as safety, controllability, suitable intensity, and suitable distribution of incident energy. See generally, "Radiation Curing", Kirk-Othmer Encyclopedia of Chemical Technology 3d Ed., Vol. 19, pp. 607–624 (1982). Preferred radiant energy sources are ultraviolet or visible light sources whose emission spectra correspond closely with the absorption range of the polymerization initiator in the ionomer cement system. For instance, sources emitting ultraviolet light at wavelengths between about 335 and 385 nm, and sources emitting visible light in the blue region at wavelengths between about 420 and 480 nm are preferred for use with the preferred ultraviolet- and visible-light-induced polymerization initiators, respectively. For polymerizing cement systems in the mouth, visible light radiation such as that provided by standard dental curing lights is particularly preferred.

Upon exposure of an ionomer cement system of the present invention to an appropriate source of radiant energy, the system may begin to cure, e.g., within about 45 seconds, and preferably within about 30 seconds. The cement generally exhibits the greatest degree of cure near its surface, where the radiant energy is most intense. The surface of the cement therefore can be cured sufficiently to allow subsequent procedures to be performed, while the interior of the cement is allowed to harden fully by means of the ongoing ionic and/or non-ionic setting reaction. Thus, if the curing step is omitted, the setting reaction will occur, ultimately resulting in the hardening of the material, even in the dark.

The ionomer cements of this invention can be used for cementation of a variety of dental prosthetic devices that will be used to provisionally replace tooth structure. For instance, these cements can be used to bond provisional crowns, bridges, inlays, onlays or veneers to tooth structure.

Bulk Shear Adhesion Test

Bulk shear adhesion of cement samples to dentin was evaluated as follows. Bovine teeth of similar age and appearance were embedded in circular acrylic disks and then ground flat and parallel to the acrylic disk using Grade 120 silicon carbide paper-backed abrasive mounted on a lapidary wheel until sufficient dentin was exposed. Further grinding and polishing of the teeth was carried out by mounting Grade 600 silicon carbide paper-backed abrasive on the lapidary wheel. During the grinding and polishing steps, the teeth were continuously rinsed with water. The polished teeth were stored in deionized water at 37° C.

After removing the polished teeth from the water, the teeth were shaken to remove excess water and then conditioned at 37° C./95% relative humidity ("RH") for 15–30 minutes or until no moisture was visible on the surface.

A mold made from a 2 mm thick Teflon™ polytetrafluoroethylene sheet with a 5 mm diameter circular hole through the sheet was clamped to each polished tooth so that the central axis of the bole in the mold was normal to the polished tooth surface. The hole in each mold was lined with a gelatin cylinder (#1 gelatin capsule; Lilly Co.) to allow easy removal. Care was taken to ensure that the hole was positioned entirely over exposed dentin (and not enamel). The hole was filled with mixed cement, trimmed flush with the mold and then allowed to cure at 37° C./95% RH for 15 minutes. The samples were then stored in deionized water at 37° C. for 24 hours.

The molds were removed shortly before testing, leaving a molded button of cement attached to each tooth. The gelatin liners had softened or dissolved, allowing for easy removal with minimal disruption of the remaining button.

Adhesive strength was evaluated by mounting the acrylic disk in a holder clamped in the jaws of an Instronr™ testing apparatus with the polished tooth surface oriented parallel to the direction of pull. A loop of 0.44 mm diameter wire was placed around the base of the cement button adjacent to the polished tooth surface. The ends of the wire were clamped in the pulling jaw of the testing apparatus, placing the bond in shear stress. The bond was stressed until it failed, using a crosshead speed of 2 mm/min. Bulk shear adhesion ("BSA") values for 5 samples of each cement were measured and the average and standard deviation ("SD") recorded.

The present invention will be further understood in view of the following examples which are merely illustrative and not meant to limit the scope of the invention. Unless otherwise indicated, all parts and percentages are by weight.

PREPARATORY EXAMPLE 1

Treated Fluoroaluminosilicate Glass

The ingredients set out below in TABLE I were mixed, melted in an are furnace at about 1350°–1450° C., poured from the furnace in a thin stream and quenched using chilled rollers to provide an amorphous single-phase fluoroaluminosilicate glass.

TABLE I

| Ingredient | Part % |
|---|---|
| $SiO_2$ | 37 |
| $AlF_3$ | 23 |
| $SrCO_3$ | 20 |
| $Al_2O_3$ | 10 |
| $Na_3AlF_6$ | 6 |
| $P_2O_5$ | 4 |

The glass was ball-milled to provide a pulverized frit with a surface area of 2.5–3.2 $m^2$/g measured using the Brunauer, Emmet and Teller (BET) method.

A silanol solution was prepared by mixing together 2.4 parts gamma-methacryloxypropyl trimethoxysilane ("A-174", Union Carbide Corp.), 12.6 parts methanol, 36.5 parts water and 0.33 parts acetic acid. The mixture was stirred magnetically for 60 minutes at ambient temperature, added to 60.8 parts of the glass powder and slurried for 30 minutes at ambient temperature. The slurry was poured into a plastic-lined tray and dried for 10 hours at 80° C. The silanol treated dried powder was sieved through a 60 micrometer mesh screen.

PREPARATORY EXAMPLE 2

Cement Forming Liquid

The ingredients set out below in TABLE II were mixed to provide a luting cement forming liquid.

TABLE II

| Ingredient | Parts |
|---|---|
| Copolymer[1] | 35 |
| HEMA | 30 |
| Water[2] | 35 |
| Tartaric Acid[3] | 0.5 |
| BHT[4] | 0.05 |

[1]Ethylenically unsaturated acidic copolymer prepared like the precipitated dry polymer of EXAMPLE 11 of U.S. Pat. No. 5,130,347.
[2]Deionized water.
[3]1-Tartaric acid.
[4]BUtylated hydroxy toluene.

The ingredients were placed in a bottle and mixed by rolling the bottle overnight. The mixed cement forming liquid was transferred to a vial with a 0.94–1.09 mm diameter dropper hole.

PREPARATORY EXAMPLE 3

Treated Zirconia:Silica Filler 25.5 Parts silica sol("LUDOX" LS, E.I. dupont de Nemours & Co.) were acidified by the rapid addition of 0.255 parts concentrated nitric acid. In a separate vessel, 12.9 parts ion-exchanged zirconyl acetate (Magnesium Elecktron Inc.) were diluted with 20 parts deionized water and the resultant solution acidified with 0.255 parts concentrated nitric acid. The silica sol was pumped into the stirred zirconyl acetate solution and mixed for one hour while filtering the stirred mixture through "CUNO" 5 micrometer and 1 micrometer filters (Commercial Intertech Corp.). The stirred, filtered mixture was further filtered though a 1 micrometer "HYTREX" filter (Osmonics, Inc.) followed by a 0.22 micrometer "BALSTRON" filter (Balston Inc.). The filtrate was poured into trays to a depth of about 25 mm and dried at 65° C. in a forced air oven for about 24 hours. The resultant dried material was removed from the oven and tumbled through a rotary tube furnace (Harper Furnace Corporation) preheated to 600° C. to provide 21 parts of calcined microparticles. The calcined microparticles were comminuted in a tumbling ball mill until all of the microparticles were less than 10 micrometers in particle diameter. 0.3 Part portions of the milled microparticles were placed in ceramic saggers and fired in an electric kiln (Harper Furnace Corporation) in air at 825° C. for 1 hour. The fired microparticles were allowed to cool in air. The cooled microparticles were slurried in hydrolyzed A-174 silane at a ratio of 11.1 parts silane to 100 parts microparticles, dried in a forced air oven and screened through a 74 micrometer mesh screen.

PREPARATORY EXAMPLE 4

Treated OX-50

A-174 (3.7 g) was added with stirring to 50 g of deionized water acidified to pH 3–3.3 by dropwise addition of trifluoroacetic acid. The resultant mixture was stirred at about 25° C. for 1 hour at which time 95 g of OX-50 were added to the mixture with continued stirring for 4 hours. The slurry was poured into a plastic-lined tray and dried at 35° C. for 36 hours. The silanol treated dried powder was sieved through a 74 micrometer mesh screen.

Example 1

Various types and amounts of adhesion reducing components were added to a mixture of the fluoroaluminosilicate glass of PREPARATORY EXAMPLE 1, 0.7% potassium persulfate, 0.2% ascorbic acid and 0.5% $TiO_2$ (TiPure, E.I. dupont de Nemours & Co.). Both the potassium persulfate and the ascorbic acid were microencapsulated in cellulose acetate butyrate prepared according to the procedure of EXAMPLE 9 of U.S. Pat. No. 5,154,762. For each run, the ingredient in the amount set out below in TABLE III was combined with the above ingredients and blended for 5 minutes in a Spex Mill (Spex Industries, Edison, N.J.).

TABLE III

| Run No. | Glass Amount (Wt. %) | Adhesion Reducing Component | Amount (Wt. %) |
|---|---|---|---|
| 1 | 97.6 | $NaH_2PO_4 \cdot 2H_2O$[1] | 1 |
| 2 | 97.6 | $NaH_2PO_4 \cdot 2H_2O$ | 1 |
| 3 | 88.6 | $NaH_2PO_4 \cdot 2H_2O$ | 10 |
| 4 | 88.6 | $Na_3PO_4 \cdot 7H_2O$[2] | 10 |
| 5 | 97.6 | $K_3PO_4 \cdot 7H_2O$[3] | 1 |
| 6 | 88.6 | $K_3PO_4 \cdot 7H_2O$ | 10 |
| 7 | 97.6 | $NH_4H_2PO_4$[4] | 1 |
| 8 | 88.6 | $NH_4H_2PO_4$ | 10 |
| 9 | 97.6 | MgO[5] | 1 |
| 10 | 88.6 | MgO | 10 |
| 11 | 88.6 | Mgo | 10 |
| 12 | 97.6 | Sodium citrate[6] | 1 |
| 13 | 88.6 | Sodium citrate | 10 |
| 14 | 69.1 | $TiO_2$[7] | 30 |
| 15 | 39.1 | $TiO_2$ | 60 |
| 16 | 68.6 | $ZrO_2:SiO_2$[8] | 30 |
| 17 | 38.6 | $ZrO_2:SiO_2$ | 60 |
| 18 | 95.4 | Cellulose[9] | 4.6 |
| 19 | 84.4 | Cellulose | 15.6 |

[1] JT Baker Chemical Co., Philadelphia, PA.
[2] EM Science, a Division of EM Industries, Gibbstown, NJ.
[3] EM Science, a Division of EM Industries, Gibbstown, NJ.
[4] Rhone-Poulenc, Shelton, CT.
[5] National Magnesium Chemicals, a Division of National Refractories & Minerals Corp., Moss Landing, CA.
[6] Pfizer, Southport, NC.
[7] TiPure, E.I. duPont de Nemours & Co.
[8] Treated Zirconia:Silica filler of PREPARATORY EXAMPLE 3.
[9] Expancel Microspheres 551, Nobel Industries, Sundsvall, Sweden.

For each run, the powder was measured using the scoop provided with the 3M™ Vitremer™ Luting Cement System and the liquid was measured in number of drops from a vial with a 0.94–1.09 mm diameter dropper hole. The powder-:liquid ("P:L") ratio for each run is indicated in TABLE IV. Luting cements were prepared by independently hand spatulating on a paper mix pad with a steel spatula for about 30 seconds the powder from each run with the cement forming liquid of PREPARATORY EXAMPLE 2.

For each luting cement sample, the BSA was determined using the Bulk Shear Adhesion Test set above.

For determination of CS and DTS, each luting cement sample was packed into a 4 mm inside diameter glass tube, capped with silicone rubber plugs and axially compressed at about 0.28 MPa for 15 minutes. Each of the samples was allowed to stand for one hour at ambient pressure, 09%+RH and 37° C. The samples were cut on a diamond saw to form cylindrical plugs 8 mm long for measurement of CS and 2 mm long for measurement of DTS. The plugs were stored in deionized water at approximately 37° C. for about 24 hours. CS and DTS values for 5 samples of each cement were measured according to ISO specification 7489 and the average recorded.

The compatibility of the provisional cement of the invention with a permanent cement ("PCC"), 3M™ Vitremer™ Luting Cement, was evaluated using bovine dentin surfaces prepared as detailed in the Bulk Shear Adhesion Test described above. Following grinding and polishing with Grade 600 silicon carbide paper-backed abrasive, the teeth were stored in 37° C. deionized water overnight. Prior to bonding, excess moisture was removed from the teeth with a damp towel. The teeth were then allowed to equilibrate at 37° C./95% RH for 15–30 minutes.

A 0.5–1.0 mm thick layer of the provisional luting cement of each run was applied to cover the prepared dentin surface. A polyethylene terephthalate film ("PET" film, 0.5 mm thickness, 3M) was placed over the cement and pressed gently by hand with a flat surface (e.g., jar bottom or microscope slide) to provide an approximately uniform layer of cement. The cement was then allowed to cure at 37° C./95% RH for 15–30 minutes. The samples were removed from the humidity chamber, the film was removed and the samples were stored in deionized water at 37° C. for 7 days.

The samples were removed from the deionized water and the provisional luting cement was removed with a scaler. The teeth were then wiped with a damp wipe to remove any remaining visible debris and rinsed with deionized water.

Excess water was removed from the samples with a damp towel and then the samples were placed in the humidity chamber for 15–30 minutes.

Rexillium™ III (Jeneric™/Pentron™, Wallingford, Conn.) was cast into rods from which 5 mm diameter buttons were cut. The buttons were sandblasted for about 20 seconds to clean and roughen the metal bonding surface. The sand and dust were blown off the metal surface. The buttons were cleaned in 200 proof ethanol in an ultrasonic bath for 10 minutes, then dried thoroughly using a paper towel.

The permanent cement was mixed according to the manufacturer's instructions and applied to the prepared Rexillium III button. The button coated with the permanent luting cement was pressed onto the dentin sample in the porthole of the humidity chamber. The sample was allowed to remain in the chamber until the permanent luting cement was set enough to remove excess cement with an explorer (about 2–3 minutes).

The cement was then allowed to cure at 37° C./95% RH for 15–30 minutes. The samples were removed from the humidity chamber and stored in deionized water at 37° C. overnight. Adhesive strength values for 5 samples of each cement were measured as described in the Bulk Shear Adhesion Test and the average recorded.

Fluoride release was measured by forming each luting cement composition into disks 20 mm in diameter and 1 mm thick. Both sides of each disk were covered with PET film and cured at 37° C./95% RH for 15 minutes. The film was then removed and the exposed samples allowed to cure for 1 hour at 37° C./95% RH.

A fluoride-selective electrode, Orion Model 96-09-00 (from Orion Research Inc., Cambridge, Mass.) was used to quantify the amount of fluoride ion released from the sample in phosphate buffer. The electrode was calibrated using Fluoride Activity Standards #940907 and #040908, a 100 parts per million ("ppm") and a 10 ppm respectively, fluoride standard fluid (both from Orion Research Inc.).

Each disk was placed in ajar of phosphate buffer having a pH of 6.8–7.0 at 25° C. Ajar of buffer solution with no disk was prepared and measured to establish a blank control. The phosphate buffer was prepared by mixing 0.7 g $KH_2PO_4$, 0.71 g $Na_2HPO_4$ and 1 liter deionized water to provide a 0.01M solution. The fluoride probe was placed in the buffer solution containing the disk on day 14 and ppm $F^-$ recorded. Micrograms of $F^-$ per gram of the cured disk were then calculated and these values were reported as a function of time of storage in the water. Fluoride release values for 3 samples of each cement were measured and the average recorded. Samples whose measured fluoride level was less than or equal to the blank control were considered to have 0 fluoride release.

Set out below in TABLE IV are the P:L ratio of the cement, the BSA, CS, DTS, PCC and fluoride release at 14 days. Run no. "Con" was a commercial glass ionomer permanent cement, 3M™ Vitremer™ Luting Cement System, mixed at a 1.6:1 weight ratio. The BSA value was the average of 75 samples and the fluoride release was at 21 days.

TABLE IV

| Run No. | P:L | BSA MPa SD | CS (MPa) | DTS (MPa) | PCC MPa SD | F Release ($\mu$g/g) |
|---|---|---|---|---|---|---|
| 1 | 3:4 | 3.9 ± 1.8 | | | 2.6 ± 0.9 | |
| 2 | 1:1 | 0.6 ± 1.0 | | | | |
| 3 | 3:4 | 0.1 ± 0.1 | 44.1 | 9.0 | 3.7 ± 2.0 | 6200* |
| 4 | 1:1 | 0.7 ± 0.6 | 73.1 | 13.8 | 3.7 ± 2.7 | 8800* |
| 5 | 3:4 | 2.2 ± 2.3 | | | | |
| 6 | 1:1 | 0.0 | | | | |
| 7 | 1:1 | 2.9 ± 1.5 | | | | |
| 8 | 3:4 | 0.0 | | | | |
| 9 | 1:1 | 3.0 ± 2.7 | | | | |
| 10 | 3:4 | 1.2 ± 0.7 | 69.7 | 12.4 | 2.8 ± 2.2 | 2100 |
| 11 | 1:1 | | 31.7 | | | |
| 12 | 3:4 | 1.9 ± 1.2 | | | | |
| 13 | 3:4 | 0.7 ± 1.4 | | | | |
| 14 | 3:4 | 4.6 ± 1.8 | | | | |
| 15 | 1:1 | 4.9 ± 0.9 | | | | |
| 16 | 1:1 | 5.2 ± 2.0 | | | | |
| 17 | 1:1 | 2.7 ± 1.8 | | | | |
| 18 | 4:3 | 0.8 ± 0.5 | | | | |
| 19 | 5:3 | 0.1 ± 0.2 | | | | |
| Com | | 4.1 ± 2.1 | 128.6 | 23.5 | | 1300 |

*Runs 3 and 4 fluoride samples disintegrated partially.

The data in TABLE IV show that runs 2–4, 6, 8, 10, 12–13, 18 and 19 show suitable BSA for use as a provisional luting cement according to the present invention.

Example 2

The ingredients in the amounts set out below in run nos. 1–53, 55–60 and 65–69 in TABLE V, along with 0.5 parts 1-tartaric acid and 0.05 parts BHT were combined in a bottle and the bottle was rolled overnight. Run nos. 54 and 61–64 contained 0.5 parts 1-tartaric acid, and 20 ppm of FD & C Yellow dye #5 (Warner-Jenkinson, St. Louis, Mo.) but no BHT.

TABLE V

| Run No. | Cement Forming Liquid (Parts) | | | Adhesion Reducing Component | Amount (Parts) |
|---|---|---|---|---|---|
| | $CP^1$ | HEMA | $H_2O^2$ | | |
| 1 | 10 | 49.5 | 31.5 | $PEG_{400}DMA^3$ | 9 |
| 2 | 10 | 36 | 45 | $PEG_{400}DMA$ | 9 |
| 3 | 10 | 36 | 45 | $PEG_{400}DMA$ | 9 |
| 4 | 35 | 20 | 35 | $PEG_{400}DMA$ | 10 |
| 5 | 41 | 0 | 41 | $PEG_{400}DMA$ | 18 |
| 6 | 41 | 0 | 41 | $PEG_{400}DMA$ | 18 |
| 7 | 35 | 10 | 35 | $PEG_{400}DMA$ | 20 |
| 8 | 25 | 20 | 35 | $PEG_{400}DMA$ | 20 |
| 9 | 10 | 36 | 27 | $PEG_{400}DMA$ | 27 |
| 10 | 35 | 0 | 35 | $PEG_{400}DMA$ | 30 |
| 11 | 35 | 0 | 35 | $PEG_{400}DMA$ | 30 |
| 12 | 10 | 22.5 | 33.8 | $PEG_{400}DMA$ | 33.8 |
| 13 | 10 | 22.5 | 33.8 | $PEG_{400}DMA$ | 33.8 |
| 14 | 15 | 10 | 35 | $PEG_{400}DMA$ | 40 |
| 15 | 15 | 10 | 35 | $PEG_{400}DMA$ | 40 |
| 16 | 15 | 10 | 35 | $PEG_{400}DMA$ | 40 |
| 17 | 10 | 5 | 50 | $PEG_{400}DMA$ | 40 |
| 18 | 10 | 13.5 | 27 | $PEG_{400}DMA$ | 49.5 |
| 19 | 25 | 0 | 25 | $PEG_{400}DMA$ | 50 |
| 20 | 10 | 0 | 30 | $PEG_{400}DMA$ | 60 |
| 21 | 10 | 0 | 30 | $PEG_{400}DMA$ | 60 |
| 22 | 10 | 13.5 | 9 | $PEG_{400}DMA$ | 67 |
| 23 | 10 | 13.5 | 9 | $PEG_{400}DMA$ | 67 |
| 24 | 10 | 0 | 10 | $PEG_{400}DMA$ | 80 |
| 25 | 10 | 0 | 10 | $PEG_{400}DMA$ | 80 |
| 26 | 10 | 0 | 10 | $PEG_{400}DMA$ | $80^4$ |
| 27 | 9 | 18.8 | 67.2 | TEGDMA | 5 |
| 28 | 10 | 30 | 55 | TEGDMA | 5 |
| 29 | 35 | 20 | 35 | TEGDMA | 10 |
| 30 | 25 | 20 | 35 | TEGDMA | 20 |
| 31 | 25 | 20 | 35 | TEGDMA | 20 |
| 32 | 35 | 5 | 35 | TEGDMA | 25 |
| 33 | 35 | 5 | 35 | TEGDMA | 25 |
| 34 | 35 | 0 | 35 | TEGDMA | 30 |
| 35 | 25 | 25 | 25 | TEGDMA | 30 |
| 36 | 10 | 40 | 10 | TEGDMA | 40 |
| 37 | 10 | 15 | 10 | TEGDMA | 65 |
| 38 | 10 | 15 | 10 | TEGDMA | 65 |
| 39 | 10 | 0 | 30 | $PEG_{400}DMA$, TEGDMA | 45, 15 |
| 40 | 10 | 0 | 30 | $PEG_{400}DMA$, TEGDMA | 45, 15 |
| 41 | 15 | 56.6 | 14.2 | Glycerol[5] | 14.2 |
| 42 | 15 | 14.2 | 56.6 | Glycerol | 14.2 |
| 43 | 30 | 25 | 30 | Glycerol | 15 |
| 44 | 30 | 25 | 30 | Glycerol | 15 |
| 45 | 30 | 25 | 30 | Glycerol | 15 |
| 46 | 10 | 15 | 60 | Glycerol | 15 |
| 47 | 10 | 60 | 15 | Glycerol | 15 |
| 48 | 25 | 25 | 25 | Glycerol | 25 |
| 49 | 15 | 28.3 | 28.4 | Glycerol | 28.3 |
| 50 | 25 | 20 | 25 | Glycerol | 30 |
| 51 | 25 | 20 | 25 | Glycerol | 30 |
| 52 | 10 | 30 | 30 | Glycerol | 30 |
| 53 | 10 | 30 | 30 | Glycerol | 30 |
| 54 | 4.3 | 27.1 | 32.4 | Glycerol | 36.2 |
| 55 | 15 | 37.8 | 9.4 | Glycerol | 37.8 |
| 56 | 10 | 40 | 10 | Glycerol | 40 |
| 57 | 10 | 40 | 10 | Glycerol | 40 |
| 58 | 15 | 21.2 | 21.2 | Glycerol | 42.6 |
| 59 | 10 | 22.5 | 22.5 | Glycerol | 45 |
| 60 | 35 | 30 | 35 | 1-Tartaric acid | 9.5 |
| 61 | 20.1 | 11.6 | 68.3 | $NaH_2PO_4$[6] | 0.1 |
| 62 | 20.1 | 11.6 | 68.3 | $NaH_2PO_4$ | 0.5 |
| 63 | 16.3 | 11.7 | 72.0 | $NaH_2PO_4$ | 1.0 |
| 64 | 16.3 | 11.7 | 72.0 | $NaH_2PO_4$ | 5.0 |
| 65 | 46.7 | 6.6 | 46.7 | $NaH_2PO_4 2H_2O$ | 13.3 |
| 66 | 46.7 | 6.6 | 46.7 | $NaH_2PO_4 2H_2O$ | 13.3 |
| 67 | 46.7 | 6.6 | 46.7 | $NaH_2PO_4 2H_2O$ | 13.3 |
| 68 | 46.7 | 6.6 | 46.7 | $NaH_2PO_4 2H_2O$ | 13.3 |
| 69 | 35 | 30 | 50 | Nalco 1034 sol[7] | 35 |

[1]Ethylenically unsaturated acidic copolymer prepared like the precipitated dry polymer of EXAMPLE 11 of U.S. Pat. No. 5,130,347.
[2]Deionized water.
[3]Polyethyleneglycol$_{400}$ dimethacrylate (Rohm-Tech, Malden, MA).
[4]Contained approximately 1 drop of yellow food dye (Schilling) in 10 g of cement forming liquid.
[5]Aldrich Chemical Company, Inc., Milwaukee, WI.
[6]JT Baker Chemical Co., Philadelphia, PA.
[7]Nalco Chemical Co., Chicago, IL.

Luting cements were prepared by mixing the liquid from each run with the glass described in EXAMPLE 1. For run nos. 1–53, 55–60 and 65–69, the powder and liquid were measured out and mixed as described in EXAMPLE 1. For run nos. 54 and 61–64, the P:L ratio was by weight. The CS, DTS, PCC and fluoride relase of the luting cement of each run was evaluated as detailed in EXAMPLE 1. The BSA for run nos. 1–53, 55–60 and 65–69 was evaluated as described in EXAMPLE 1. For run nos. 54 and 61–64, the general procedure described in EXAMPLE 1 was followed, except that instead of conditioning in a humidity chamber, the ground and polished teeth were rinsed with water, gently air dried and then covered with a one µl film of deionized water prior to clamping the Teflon mold in place.

Adhesion of the provisional luting cement of the invention to 3M™ Vitremer™ Core Buildup/Restorative System ("AV") was evaluated using the general procedure of the Bulk Shear Adhesion Test described above, except that Vitremer core buildup/restorative, instead of dentin, was used as the substrate. Vitremer core buildup/restorative was mixed according to the manufacturer's instructions, loaded into a 1 cm diameter Delrin™ mold, pressed flat with a PET film against a glass microscope slide and light cured according to the manufacturer's instructions. The core buildup/restorative substrates were then ground using 600 grit silicon carbide paper-backed abrasive and stored in deionized water until used on the same day. The substrates were removed from the water, gently dried with filtered compressed air and covered with a film of one µl of deionized water. The Teflon mold was clamped to the Vitremer substrate and the procedure detailed in the Bulk shear Adhesion Test followed.

Ease of removability ("ER") of a crown adhered to dentin with the provisional luting cement of the invention was evaluated using six extracted human molars which were autoclaved and mounted in epoxy vertically by the root so that the entire crown and a small portion of the root was exposed. Notches were cut in the root to improve retention. The teeth were prepared using standard equipment and techniques to accept a full coverage crown. 3M™ ion™ Iso-Form™ Crowns were selected to fit each tooth. The teeth were immediately placed in and stored in 37° C. water for 7 days.

On the seventh day, the crowns were removed from the 37° C. water and the epoxy mount secured in a vise. The crown was gripped with a Kelly Hemostat (Patterson Dental Co., Minneapolis, Minn.) and pulled off of the tooth. The ease of removal for the luting cement of the invention was compared to that of a commercial temporary cement, Temp Bond (Kerr Manufacturing, Romulus, Mich.). A rating of "A" signified removal at least as easy as Temp Bond cement, "B" signified removal more difficult than Temp Bond cement, but still clinically acceptable and "F" signified removal too difficult to be clinically acceptable. The above described prepared human molars were used for each of the luting cements evaluated. Prior to evaluation of a second luting cement, any remaining cement was removed and the tooth surfaces were freshened with a diamond burr.

Set out below in TABLE VI are the P:L mix ratio of the cement, the BSA, CS, DTS, PCC, fluoride release at 14 days, AV and ER. Run no. "Con" was a commercial glass ionomer permanent cement, 3M™ Vitremer™ Luting Cement System, mixed at a 1.6:1 weight ratio. The BSA value was the average of 75 samples and the fluoride release was at 21 days.

TABLE VI

| Run No. | P:L | BSA MPa SD | CS (MPa) | DTS (MPa) | PC MPa SD | F (µg/g) | AV MPa SD | ER |
|---|---|---|---|---|---|---|---|---|
| 1 | 4:3 | 0.1 ± 0.2 | 110.4 | | | | | F |
| 2 | 1:1 | 0.5 ± 0.4 | | | | | | B |
| 3 | 1:1 | 0.1 ± 0.1 | 52.4 | | | | | |
| 4 | 3:5 | 4.3 ± 2.2 | | | | | | |
| 5 | 3:4 | 2.7 ± 2.5 | | | | | | |
| 6 | 1:1 | 1.0 ± 0.9 | | | | | | |
| 7 | 2:4 | 3.9 ± 2.6 | | | | | | |
| 8 | 3:5 | 2.7 ± 1.5 | | | | | | |
| 9 | 4:3 | 2.8 ± 1.5 | 105.5 | | | | | F |
| 10 | 3:5 | 3.0 ± 1.8 | | | | | | |
| 11 | 1:1 | | 102.1 | | | 1300 | | |
| 12 | 1:1 | 0.6 ± 0.8 | | | | | | F |
| 13 | 1:1 | 0.3 ± 0.5 | 64.1 | | | | | |
| 14 | 3:5 | 0.6 ± 0.9 | | | 3.8 ± 1.9 | 800 | | B |
| 15 | 1:1 | 2.5 ± 1.9 | | | | | | |
| 16 | 3:4 | 1.2 ± 1.4 | 56.6 | | | | | |
| 17 | 1:1 | 0 | 31.7 | 6.9 | | | 2.2 ± 0.6 | A |
| 18 | 1:1 | 0.2 ± 0.2 | 71.7 | | | | | F |
| 19 | 1:1 | 0.4 ± 0.3 | 71.7 | 13.1 | | | | F |
| 20 | 1:1 | 1.1 ± 0.8 | 56.6 | | | 600 | | |
| 21 | 1:1 | 0.2 ± 0.3 | | | | | | |
| 22 | 1:1 | 1.1 ± 1.5 | | | | | | |
| 23 | 4:3 | 0.5 ± 0.5 | 90.3 | | | | | |
| 24 | 4:3 | 0.4 ± 0.3 | | | | | | A |
| 25 | 4:3 | 0.5 ± 0.8 | 84.8 | | | | | |
| 26 | 4:3 | 0.6 ± 0.6 | 111.7 | | | | | A |
| 27 | 1:1 | | | | | | 0.3 ± 0.5 | A |
| 28 | 1:1 | | | | | | 1.3 ± 0.7 | B |
| 29 | 3:5 | 2.7 ± 1.5 | | | | | | |
| 30 | 3:5 | 2.2 ± 0.4 | | | | | | |
| 31 | 1:1 | 1.5 ± 1.6 | 94.5 | | | 1100 | | |
| 32 | 2:4 | 2.3 ± 1.7 | | | | | | |
| 33 | 3:5 | 2.2 ± 1.3 | | | | | | |
| 34 | 2:4 | 3.1 ± 1.9 | | | | | | |
| 35 | 1:1 | 2.9 ± 1.2 | | | | | | |
| 36 | 1:1 | 2.3 ± 1.4 | | | | | | |

TABLE VI-continued

| Run No. | P:L | BSA MPa SD | CS (MPa) | DTS (MPa) | PC MPa SD | F (µg/g) | AV MPa SD | ER |
|---|---|---|---|---|---|---|---|---|
| 37 | 4:3 | 0 | 52.4 | | | | 0.8 ± 0.3 | B |
| 38 | 4:3 | | | | | | 3.3 3≡ 0.5 | |
| 39 | 4:3 | 0.1 ± 0.3 | | | | | | A |
| 40 | 4:3 | 0 | 76.6 | | | | 4.2 ± 1.1 | |
| 41 | 4:3 | 1.3 ± 2.0 | | | | | | |
| 42 | 3:4 | 0 | | | | | 0.3 ± 0.6 | |
| 43 | 3:5 | 0.7 ± 9.6 | | | 4.7 ± 2.9 | | | |
| 44 | 3:4 | 2.7 ± 2.5 | 61.4 | | | | | |
| 45 | 1:1 | 1.9 ± 1.4 | | | | 1900 | | |
| 46 | 1:1 | 0.3 ± 0.4 | 2.1 | | | 2090 | | A |
| 47 | 1:1 | 0.3 ± 0.4 | 31.7 | | | 1450 | | B |
| 48 | 1:1 | 0.6 ± 0.5 | 33.1 | | | 2400 | | |
| 49 | 1:1 | 0.1 ± 0.3 | | | | | 2.6 ± 0.3 | |
| 50 | 3:5 | 0.9 ± 1.0 | | | | | | |
| 51 | 1:1 | 0.6 ± 0.6 | 27.6 | | 2.9 ± 1.5 | | | |
| 52 | 1:1 | 0.3 ± 0.3 | 29.7 | | | 2040 | 1.9 ± 0.2 | A |
| 53 | 1:1 | | | | | | 2.0 ± 0.3 | |
| 54 | 1.6:1 | 0.0 ± 0.1 | 9.0 | 2.1 | | | 0.4 ± 0.1 | |
| 55 | 1:1 | 0 | 71.0 | 13.8 | | | | |
| 56 | 1:1 | 0.6 ± 0.7 | 21.4 | | 2.4 ± 1.3 | 1070 | | F |
| 57 | 1:1 | 0.6 ± 0.3 | 18.6 | | | | | |
| 58 | 1:1 | 0.9 ± 1.0 | 33.1 | 9.0 | | | | B |
| 59 | 1:1 | 0.1 ± 0.1 | 24.8 | 5.5 | | | 1.0 ± 0.2 | A |
| 60 | 1:1 | 3.1 ± 0.6 | | | | | | |
| 61 | 1.5:1 | | | | | | | |
| 62 | 1.5:1 | | | | | | | |
| 63 | 1.5:1 | | | | | | | A |
| 64 | 1.5:1 | | | | | | | |
| 65 | 1:2 | 0 | 43.5 | | 5.5 ± 3.7 | | | |
| 66 | 1:1 | 1.6 ± 1.4 | 71.7 | | 4.1 ± 3.3 | 7400* | | |
| 67 | 1:1 | 0.1 ± 0.2 | | | | 4800* | | |
| 68 | 3:5 | 0.3 ± 0.3 | | | | | | |
| 69 | 1:1 | 3.5 ± 2.7 | 126.9 | | | | | |
| Con | | 4.1 ± 2.1 | 128.6 | 23.5 | | 1300 | | |

*Runs 66 and 67 fluoride samples partially disintegrated

The data in TABLE VI show that runs 1–3, 6, 12–14, 16–28, 31, 37, 39–59, 63 and 65–68 were suitable for use as provisional luting cements according to the present invention. Runs 17, 22, 24, 26, 27, 39, 42, 46, 47, 52, 55, 58, and 59 are preferred. Runs 26, 27, 42 and 46 are especially preferred.

Example 3

The ingredients in the amounts set out below in run nos. 1–17 and 30–37 in TABLE VII, along with 0.5 parts 1-tartaric acid and 0.05 parts BHT were combined in a bottle and the bottle was rolled overnight. Run no. 18 contained BHT, but no 1-tartaric acid. Run nos. 20–29 contained 1-tartaric acid and 20 ppm of FD & C yellow Dye #5, but no BHT. Run nos. 19 and 26 contained no 1-tartaric acid and no BHT. Run nos. 27 and 29 contained a total of 2 parts 1-tartaric acid and run no. 28 contained a total of 1 part 1-tartaric acid.

TABLE VII

| Run No. | Cement Forming Liquid (Parts) | | |
|---|---|---|---|
| | CP[1] | HEMA[2] | H$_2$O[3] |
| 1 | 50 | 0 | 50 |
| 2 | 30 | 0 | 70 |
| 3 | 10 | 0 | 90 |
| 4 | 40 | 20 | 40 |
| 5 | 24 | 20 | 56 |
| 6 | 8 | 20 | 72 |
| 7 | 8 | 20 | 72 |
| 8 | 30 | 40 | 30 |
| 9 | 18 | 40 | 42 |
| 10 | 6 | 40 | 54 |
| 11 | 13.5 | 55 | 31.5 |
| 12 | 10 | 55 | 35 |
| 13 | 15 | 70 | 15 |
| 14 | 10 | 70 | 20 |
| 15 | 10 | 30 | 60 |
| 16 | 10 | 30 | 60 |
| 17 | 18 | 11 | 71 |
| 18 | 10 | 30 | 60 |
| 19 | 13.3 | 39.8 | 46.9 |
| 20 | 20.8 | 10.3 | 68.9 |
| 21 | 23.8 | 13.3 | 62.9 |
| 22 | 21.5 | 8.8 | 69.7 |
| 23 | 20.1 | 11.6 | 68.3 |
| 24 | 15.5 | 19.0 | 65.5 |
| 25 | 16.3 | 11.7 | 72.0 |
| 26 | 16.3 | 11.7 | 72.0 |
| 27 | 16.3 | 11.7 | 72.0 |
| 28 | 20.1 | 11.6 | 68.3 |
| 29 | 20.1 | 11.6 | 68.3 |
| 30 | 15 | 30 | 35 |
| 31 | 35 | 15 | 35 |
| 32 | 35 | 15 | 35 |
| 33 | 35 | 15 | 35 |
| 34 | 35 | 15 | 35 |
| 35 | 35 | 15 | 35 |
| 36 | 35 | 5 | 35 |
| 37 | 35 | 5 | 35 |

[1]Ethylenically unsaturated acidic copolymer prepared like the precipitated dry polymer of EXAMPLE 11 of U.S. Pat. No. 5,130,347.
[2]Rohm-Tech, Malden, MA.
[3]Deionized water.

Luting cements were prepared by mixing the liquid from each run with the glass of EXAMPLE 1. For run nos. 1–19 and 30–37, the powder and liquid were measured out and mixed as described in EXAMPLE 1. For run nos. 20–29, the P:L ratio was by weight. The CS, DTS, PCC and fluoride relase of the luting cement of each run was evaluated as detailed in EXAMPLE 1. For run nos. 1–19 and 30–37, the BSA was evaluated as detailed in EXAMPLE 1. For run nos. 20–29, the modification of the BSA test described in EXAMPLE 2 for run nos. 54 and 61–64 was followed. The AV and ER were evaluated as described in EXAMPLE 2.

Set out below in TABLE VIII are the P:L mix ratio of the cement, the BSA, CS, DTS, PCC, fluoride release at 14 days, AV and ER. Run no. "Con" was a commercial glass ionomer permanent cement, 3M™ Vitremer™ Luting Cement System, mixed at a 1.6:1 weight ratio. The BSA value was the average of 75 samples and the fluoride release was at 21 days.

than 2:00 minutes via this method were allowed to set at ambient temperatures.

The bulk shear adhesion to enamel ("AE") of the cements of run nos. 23, 24 and 27 were evaluated using the procedure describe in the Bulk Shear Adhesion Test described above, except that the enamel, instead of the dentin, was prepared as described and the teeth were not conditioned in the humidity chamber, but instead were rinsed with water, dried with filtered compressed air, covered with a film of one μl of deionized water and used immediately. The results are set out in TABLE VIIIa below.

TABLE VIIIA

| Run no. | Set Time (Sec.) | AE MPa SD |
|---|---|---|
| 20 | 90 | |
| 21 | 90 | |
| 22 | 93 | |

TABLE VIII

| Run No. | P:L | BSA MPa SD | CS (MPa) | DTS (MPa) | PC MPa SD | F (μg/g) | AV MPa SD | ER |
|---|---|---|---|---|---|---|---|---|
| 1 | 1:1 | 2.5 ± 1.0 | | | | | | |
| 2 | 1:1 | 0.4 ± 0.4 | | | | | | |
| 3 | 1:1 | 0.1 ± 0.2 | | | | | | |
| 4 | 1:1 | 2.8 ± 2.9 | | | | | | |
| 5 | 1:1 | 1.4 ± 1.2 | | | | | | |
| 6 | 1:1 | 0.05 | 30.3 | | | 1950 | 0.7 ± 0.4 | A |
| 7 | 1:1 | | | | | | 0.4 ± 0.4 | |
| 8 | 1:1 | 3.0 ± 1.1 | | | | | | |
| 9 | 1:1 | 1.4 ± 1.4 | | | | | 3.0 ± 3.3 | |
| 10 | 1:1 | 0.5 ± 0.5 | 9.7 | | | | 1.3 ± 0.4 | A |
| 11 | 3:5 | 1.1 ± 0.7 | | | | | | |
| 12 | 4:3 | 1.0 ± 0.4 | 76.6 | | 5.1 ± 3.2 | 800 | | F |
| 13 | 3:5 | 3.4 ± 1.7 | | | | | | |
| 14 | 3:5 | 2.2 ± 1.4 | | | | | | |
| 15 | 1:1 | 0.1 ± 0.2 | 66.2 | 14.5 | | | 0.6 ± 0.6 | A |
| 16 | 1:1 | | | | | | | |
| 17 | 1:1 | | | | | | 1.2 ± 1.0 | A |
| 18 | 1:1 | 0.2 ± 0.3 | 26.2 | 5.5 | | | 0.2 ± 0.4 | F |
| 19 | 1:1 | 0.2 ± 0.3 | 50.3 | | | | 1.2 ± 0.2 | B |
| 20 | 1.5:1 | 0.1 ± 0.3 | 26.2 | 5.5 | | | 1.4 ± 0.9 | |
| 21 | 1.5:1 | 0.2 ± 0.2 | 38.61 | 9.0 | | | 1.8 ± 1.2 | |
| 22 | 1.4:1 | 0.2 ± 0.2 | 24.2 | 4.8 | | | 0.7 ± 0.7 | |
| 23 | 1.5:1 | 0.1 ± 0.3 | 3.4 | | 1.6 ± 2.9 | 2400 | 2.0 ± 0.4 | A |
| 24 | 1.5:1 | 0.3 ± 0.3 | 2.9 | | | 2400 | 1.3 ± 0.8 | |
| 25 | 1.5:1 | 0.2 ± 0.3 | 2.2 | | | 2840 | 0.9 ± 0.5 | A |
| 26 | 1.5:1 | | | | | | | |
| 27 | 1.5:1 | | | | | | | |
| 28 | 1.5:1 | | | | | | | |
| 29 | 1.5:1 | | | | | | | |
| 30 | 3:5 | 2.1 ± 1.8 | | | | | | |
| 31 | 3:5 | 0.0 | 129.7 | | | 1100 | | |
| 32 | 3:5 | 1.1 ± 0.6 | | | | | | |
| 33 | 1:1 | 2.8 ± 2.7 | | | | | | |
| 34 | 1:1 | 5.2 ± 2.4 | | | | | | |
| 35 | 3:5 | 2.1 ± 1.2 | | | | | | |
| 36 | 1:1 | 2.1 ± 1.1 | 98.6 | | 3.9 ± 4.0 | 1000 | | |
| 37 | 3:5 | 2.8 ± 1.5 | | | | | | |
| Con | | 4.1 ± 2.1 | 128.6 | 23.5 | | 1300 | | |

Set out in TABLE VIIIa are set times for the provisional luting cements of run nos. 20–29 in TABLE VIII. Set times were tested according to ISO standard DIS 9917, using a 400 g indenter. Approximately 1 minute and 30 seconds were required to mix the cement, transfer it to the mold specified in the ISO standard, and place the mold in a 37° C. oven (also specified in the ISO standard). The set time in TABLE VIIIa was the time in seconds from the start of mixing the cement to the time the cement had set. Samples that set faster TABLE VIIIA-continued

| Run no. | Set Time (Sec.) | AE MPa SD |
|---|---|---|
| 23 | 100 | 1.2 ± 1.1 |
| 24 | 97 | 0.7 ± 0.8 |
| 25 | 87 | |

TABLE VIIIA-continued

| Run no. | Set Time (Sec.) | AE MPa SD |
|---|---|---|
| 26 | 70 | |
| 27 | 93 | 0.6 ± 0.5 |
| 28 | 113 | |
| 29 | 107 | |

The cement of run no. 23 was further evaluated in terms of its adhesion to various substrates.

Adhesion to 3M™ Restorative Z100 ("Z100", 3M) was evaluated using the general procedure of the Bulk Shear Adhesion Test described above, except that Z100, instead of dentin, was used as the substrate. Z100 was pressed into 9 mm diameter Teflon molds and light cured for 30 seconds. The disks were mounted in epoxy, ground using 120 and 240 grit silicon carbide paper-backed abrasive and stored in deionized water until used. The substrates were removed from the water, gently dried with filtered compressed air and covered with a film of one µl of deionized water. The Teflon mold was clamped to the Z100 substrate and the procedure detailed in the Bulk Shear Adhesion Test followed.

Adhesion to 3M™ TempCare™ Light Cure Temporary System ("TempCare", Shade A2, 3M) was evaluated using the general procedure of the Bulk Shear Adhesion Test described above. The TempCare substrate was prepared by loading the material into 1.25 cm diameter aluminum molds. The top and bottom of the molds were covered with PET film and pressed flat. The top film was removed at 4:00 minutes from the beginning of mold filling. The material was cured for 30 seconds using a Visilux 2 curing light. The disks were used for luting cement bonding on the same day as they were prepared. The cements were bonded to the air cured side of the disk. The Teflon mold was clamped to the TempCare substrate and the procedure detailed in the Bulk Shear Adhesion Test followed.

Substrates of Espe Protemp™ II Bis-acryl Composite for Temporary Crowns and Bridges ("Protemp", Espe-Premier Sales Co., Norristown, Pa.), Trim™ II Temporary Resin Acrylic ("Trim", Harry J. Boswath Co., Skokie, Ill.) and Jet Acrylic Self Curing Resin ("Jet", Lang Dental Manufacturing Co., Wheeling, Ill.) were independently prepared using the substrate procedure described for TempCare, except that the top PET film was removed at 4:00 minutes from the beginning of mixing and the materials were allowed to cure for 10 minutes. The Teflon mold was independently clamped to each substrate and the procedure detailed in the Bulk Shear Adhesion Test followed. The BSA values for the substrates is set out below in TABLE VIIIb.

TABLE VIIIB

| Substrate | BSA MPa SD |
|---|---|
| Z100 | 0.7 ± 1.2 |
| TempCare | 0.0 ± 0.0 |
| Protemp | 0.4 ± 0.4 |
| Trim | 0.0 ± 0.0 |
| Jet | 0.0 ± 0.0 |

The data in TABLES VIII, VIIIa and VIIIb show runs 2, 3, 5, 6, 9–12, 15, 17–25, 31, 32, were suitable for use as provisional luting cement according to the present invention. Runs 6, 10, 17, 19, 23–25, and 20–22 are preferred. Runs 6, 10, 17, 20, 23, 25, are especially preferred. Runs 6. 10, 23 are most particularly preferred.

Example 4

The ingredients set out below in TABLE IX were combined to form a Paste I.

TABLE IX

| | Weight % | |
|---|---|---|
| Ingredients | Run No. 1 | Run No. 2 |
| Glass of PREP. EX. 1 | 70 | 68 |
| Deionized water | 21 | 16.5 |
| Glycerol[1] | 9 | 15.5 |
| Potassium persulfate[2] | 0.45 | 0.45 |
| Ascorbic acid[2] | 0.45 | 0.45 |

[1]Aldrich Chemical Company, Inc., Milwaukee, Wi.
[2]Microencapsulated in cellulose acetate butyrate prepared according to the procedure of EXAMPLE 9 of U.S. Pat. No. 5,154,762.

The ingredients set out below in TABLE X were combined to form a Paste II.

TABLE X

| | Weight % | |
|---|---|---|
| Ingredients | Run No. 1 | Run No. 2 |
| HEMA | 67 | 37.4 |
| Copolymer[1] | 33 | 18.7 |
| Deionized water | — | 42.0 |
| Methyl cellulose[2] | — | 1.9 |

[1]Ethylenically unsaturated acidic copolymer prepared like the precipitated dry polymer of EXAMPLE 11 of U.S. Pat. No. 5,130,347.
[2]Aldrich Chemical Company, Inc., Milwaukee, WI.

For Run no. 1, Paste I and Paste II were mixed at a weight ratio of 7.7:1. For Run no. 2, Paste I and Paste II were mixed at a weight ratio of 4.5:1. The BSA for each luting cement was determined using the Bulk Shear Adhesion Test set out above. The BSA for both resultant luting cements was 0. These cements were suitable for use as provisional luting cements according to the present invention.

Example 5

The ingredients set out below in TABLE XI were combined to form a Paste I.

TABLE XI

| Ingredients | Parts |
|---|---|
| Glass of PREP. EX. 1 | 77 |
| GDMA[1] | 19 |
| Lithium toluene sulfinate | 2 |
| Aerosil R972[2] | 2 |
| EDMAB[3] | 0.75 |
| Camphorquinone | 0.25 |

[1]1,3-Glycerol dimethyacrylate (Rohm Tech, Inc., Malden, MA).
[2]Fumed silica (Degussa).
[3]Ethyl-4-dimethyl amino benzoate.

The ingredients set out below in TABLE XII were combined to form a Paste II.

TABLE XII

| Ingredients | Weight % |
|---|---|
| Filler of PREP. EX. 3 | 52 |
| Copolymer* | 20 |

TABLE XII-continued

| Ingredients | Weight % |
| --- | --- |
| Deionized wtaer | 12 |
| GDMA | 7 |
| 1-Tartaric acid | 7 |
| Aerosil R972 | 2 |

*Ethylenically unsaturated acidic copolymer prepared like the precipitated dry polymer of EXAMPLE 11 of U.S. Pat. No. 5,130,347.

Paste I and Paste II were mixed at a weight ratio of 1.15:1. The BSA for the luting cement was evaluated using bovine dentin surfaces prepared as detailed in the Bulk Shear Adhesion Test described above with the following exceptions. The ground and polished teeth were rinsed with water and used immediately. The luting cement in the mold was light cured for 40 seconds using a 3M™ Visilux™ 2 Visible Light Curing Unit. The light cured samples were then stored in tap water at 37° C. for 24 hours. The BSA for the luting cement was 1.6±3.1.

Example 6

The ingredients set out below in TABLE XIII were combined and melted in a manner similar to that of the glass of PREPARATORY EXAMPLE 1.

TABLE XIII

| Ingredients | Parts |
| --- | --- |
| $SiO_2$ | 18.22 |
| $Al_2O_3$ | 10.60 |
| $P_2O_5$ | 2.60 |
| $AlF_3$ | 11.00 |
| $Na_2AlF_6$ | 5.88 |
| MgO | 1.00 |
| $CaF_2$ | 12.50 |
| $La_2O_3$ | 38.20 |

The glass (300 g) in TABLE XIII was charged into a 20 l mill jar with 5200 g of 12.5 mm×12.5 mm $Al_2O_3$ rods and 0.5% 200 proof ethanol and milled at 60 rpm for 4 hours.

The ingredients set out below in TABLE XIV were combined to form a Paste I forming vehicle.

TABLE XIV

| Ingredients | Weight % |
| --- | --- |
| Water[1] | 95.79 |
| Guar CMHP[2] | 1 |
| Sorbitol[3] | 3 |
| m-Paraben | 0.18 |
| p-Paraben | 0.03 |

[1]Boiled and cooled distilled water.
[2]Carboxymethylhydroxypropyl Guar, a high molecular weight carbohydrate thickener.
[3]Humectant.

The ingredients in TABLE XIV were mixed for 30 seconds in a Waring blender. Paste I compositions were prepared by combining the glass of TABLE XIII with various amounts of zinc oxide (N.J. ZnO U.S.P., not calcined) and then combining the glass/ZnO with the vehicle of TABLE XIV. Set out below in TABLE XV are the Paste I formulations.

TABLE XV

| Ingredients | Paste I Formulations | | | | | | |
| --- | --- | --- | --- | --- | --- | --- | --- |
| (Wt. %) | a | b | c | d | e | f | g |
| Glass | 75 | 71.25 | 67.5 | 63.75 | 56.25 | 37.5 | 0 |
| ZnO | 0 | 3.75 | 7.5 | 11.25 | 18.75 | 37.5 | 100 |
| Vehicle | 25 | 25 | 25 | 25 | 25 | 25 | 25 |

Paste II was prepared by concentrating Goodrite 2,000 molecular weight polyacrylic acid to 90% solids.

Set out below in TABLE XVI are the mix ratio of Paste I:Paste II by weight and the set times for each resultant cement. Set time evaluation was determined using the procedure set out in EXAMPLE 3.

TABLE XVI

| Paste I:<br>Paste II Mix | Cement Set Time (Minutes) | | | | | | |
| --- | --- | --- | --- | --- | --- | --- | --- |
| Ratio | a | b | c | d | e | f | g |
| 1:1 | 60+ | 60+ | 60+ | 60+ | 60+ | 10.5 | 1 |
| 2:1 | 27 | 26 | 13.5 | 13 | 13 | 2 | 0.5 |
| 3:1 | 16 | 14 | 5 | 4.5 | 4.5 | 1.5 | — |
| 4:1 | 12 | 10.5 | 2.5 | 2.5 | 2.5 | — | — |
| 5:1 | 9 | 5.5 | 2 | 2 | 2 | — | — |
| 6:1 | 7 | 4.5 | 1.5 | 1.5 | 1.5 | — | — |

CS was determined for the Paste Ic:Paste II luting cements using the procedure detailed in EXAMPLE 1. Set out below in TABLE XVII are the Paste Ic:Paste II mix ratio by weight and the CS for each resultant luting cement.

TABLE XVII

| Paste Ic:Paste II<br>Mix Ratio | CS<br>(MPa) |
| --- | --- |
| 1:1 | 14.6 |
| 2:1 | 14.1 |
| 3:1 | 13.4 |
| 4:1 | 13.3 |
| 5:1 | 10.5 |
| 6:1 | 6.1 |

Using the procedure detailed in EXAMPLE 1, CS was determined for the Paste Ia,b,d,e and f:PasteII luting cements at a 3:1 weight ratio of Paste I:Paste II. Set out below in TABLE XVIII are the Paste I:Paste II formulations and the CS for each resultant luting cement.

TABLE XVIII

| Paste II | CS<br>(MPa) |
| --- | --- |
| Paste Ia | 19.0 |
| Paste Ib | 18.3 |
| Paste Id | 19.7 |
| Paste Ie | 24.8 |
| Paste If | 30.7 |

Example 7

A commercially available glass ionomer permanent cement, ESPe™ Ketac-Cem™ Radiopaque Polymaleinate Glass Ionomer Cement (Espe-Premier Sales Corp., Norristown, Pa.), was modified using the method of the invention to provide a provisional glass ionomer luting cement. For run nos. 1 and 2, the adhesion reducing component was added to the powder and for run nos. 3 and 4, the adhesion reducing component was added to the liquid. Run no. 5 was the permanent cement unmodified. For each run, the powder and liquid were mixed according to the manufacturer's instructions.

Set out below in TABLE XIX are the adhesion reducing component added to each run and the BSA values of each cement determined using the procedure set out above in the Bulk Shear Adhesion Test.

TABLE XIX

| Run no. | Adhesion Reducing Component (Amount, %) | BSA Mpa SD |
|---|---|---|
| 1 | MgO (10%) | 1.3 ± 0.4 |
| 2 | $NaH_2PO_4.2H_2O$ (10%) | 0.0 |
| 3 | $NaH_2PO_4.2H_2O$ (10%) | 0.4 ± 0.9 |
| 4 | Glycerol (15%) | 2.8 ± 2.0 |
| 5 | — | 2.3 ± 0.6 |

The data in TABLE XIX show runs 1–3 are suitable for use as provisional luting cements according to the present invention. These runs demonstrate modification of permanent conventional glass ionomer cement to make a provisional cement.

Example 8

Various types and amounts of adhesion reducing components were added to the luting cement forming liquid of PREPARATORY EXAMPLE 2. For each run, the ingredient in the amount set out below in TABLE XX was combined with the liquid of PREPARATORY EXAMPLE 2 in a bottle and the bottle was rolled overnight.

TABLE XX

| Run No. | Cement Forming Liquid (Wt. %) | Adhesion Reducing Component | Amount (Wt. %) |
|---|---|---|---|
| 1 | 99 | $NaH_2PO_4.2H_2O^1$ | 1 |
| 2 | 90 | $NaH_2PO_4.2H_2O$ | 10 |
| 3 | 99 | $Na_2HPO_4^2$ | 1 |
| 4 | 90 | $Na_3PO_4.12H_2O^3$ | 10 |
| 5 | 90 | $Na_3PO_4.12H_2O$ | 10 |
| 6 | 90 | $Na_3PO_4.12H_2O$ | 10 |
| 7 | 99 | $NaHCO_3^4$ | 1 |
| 8 | 95 | NaOH | 5 |

[1]JT Baker Chemical Co., Philadelphia, PA.
[2]MCB Manufacturing Chemicals, Inc., Associate of E. Merck, Darmstadt, Germany.
[3]EM Science, a Division of EM Industries, Gibbstown, NJ.
[4]MCB Manufacturing Chemicals, Inc., Associate of E. Merck, Darmstadt, Germany.

Luting cements were prepared by mixing the liquid from each run with the glass described in EXAMPLE 1. For each run, the powder and liquid were measured out and mixed as described in EXAMPLE 1. The BSA, CS, DTS, PCC and fluoride release of the luting cement of each run was evaluated as detailed in EXAMPLE 1.

Set out below in TABLE XXI are the P:L mix ratio of the cement, the BSA, CS, DTS, PCC and fluoride release at 14 days. Run no. "Con" was a commercial glass ionomer permanent cement, 3M™ Vitremer™ Luting Cement System, mixed at a 1.6:1 weight ratio. The BSA value was the average of 75 samples and the fluoride release was at 21 days.

TABLE XXI

| No. | P:L | BSA Mpa SD | CS (MPa) | DTS (MPa) | PCC MPa SD | F Release (µg/g) |
|---|---|---|---|---|---|---|
| 1 | 2:4 | 2.6 ± 2.0 | | | | |
| 2 | 1:1 | | 122.1 | | 3.8 ± 3.4 | |
| 3 | 2:4 | 3.2 ± 1.0 | | | | |
| 4 | 2:4 | 0.8 ± 0.4 | | | | |
| 5 | 1:1 | 3.4 ± 1.7 | 112.4 | | | |
| 6 | 1:1 | 2.5 ± 3.4 | | | | |
| 7 | 3:4 | 3.5 ± 1.4 | | | | |
| 8 | 1:2 | 0 | | | 5.3 ± 3.4 | |
| Con | | 4.1 ± 2.1 | 128.6 | 23.5 | | 1300 |

The data in TABLE XXII show runs 4 and 8 were suitable for use as provisional luting according to the present invention.

Example 9

The ingredients set out below in TABLE XXII were placed in a bottle and mixed by rolling the bottle overnight to provide a cement forming liquid.

TABLE XXII

| Ingredient | Wt. % |
|---|---|
| Copolymer[1] | 35 |
| HEMA | 25.85 |
| Water[2] | 25.85 |
| GDMA[3] | 12 |
| $(C_6H_5)_2I^+PF_6^-$ | 1.0 |
| Camphorquinone | 0.25 |
| BHT | 0.05 |

[1]Ethylenically unsaturated acidic copolymer prepared like the precipitated dry polymer of EXAMPLE 11 of U.S. Pat. No. 5,130,347.
[2]Deionized water.
[3]1,3-Glycerol dimethacrylate (Rohm Tech, Inc., Malden, MA).

Various amounts of potassium persulfate ("PP") and ascorbic acid ("AA") were added to glass prepared as detailed in PREPARATORY EXAMPLE 1 with the exception that the silanol treated dried powder was sieved through a 74 micrometer mesh screen. Both the potassium presulfate and the ascorbic acid were microencapsulated in cellulose acetate butyrate prepared according to the procedure of EXAMPLE 9 of U.S. Pat. No. 5,154,762.

For each run, the ingredients in the amounts set out below in TABLE XXIII were combined and blended by tumbling with 3–5 12.7 mm cylindrical burundum media for about 18 hours.

The shear adhesion of each luting cement sample in a thickness approximating that of a cavity liner was evaluated using bovine dentin surfaces prepared as detailed in the Bulk Shear Adhesion Test described above. The ground and polished teeth were rinsed with water and used immediately. The dentin surface was dried with oil-free compressed air. A 5 mm diameter hole was cut in the center of a 19 mm square of 0.23 mm thick 3M™ 401 Double Coated Paper Tape (Industrial Tape and Specialties Division, 3M). The backing was removed from the tape and the tape was placed in the center of the exposed dry dentin surface.

Under safelight conditions, the blended powder of each run was independently hand spatulated, following the procedure of EXAMPLE 1, with the cement forming liquid of TABLE XXII in at 1.4:1 weight ratio. Each cement formulation was spread over the exposed dentin surface with a spatula until the cement was the approximate thickness of the surrounding tape. The samples were placed in a 37°

C./85% RH chamber for 10 minutes. The resin and liquid from the 3M™ Scotchbond™ Dual Cure Dental Adhesive were mixed according to the manufacturer's instructions, the mixture applied twice to the set liner and air dried for 3 seconds.

A mold made from a 2 mm thick PET sheet with a 5 mm diameter circular hole through the sheet was clamped to each specimen and the procedure detailed in the Bulk Shear Adhesion Test was followed as described above, except that the hole was filled with a 1:1 by volume mixture of paste A and paste B of 3M™ P-10™ Resin Bonded Ceramic and allowed to cure at 37° C./85% RH for 10 minutes. The specimens were then stored in tap water at 37° C. for 24 hours. Adhesive strength was determined according to the procedure of the Bulk shear Adhesion Test set out above.

TABLE XXIII

| Run No. | Glass Amount (Wt. %) | Amount (Wt %) PP | Amount (Wt %) AA | BSA Mpa SD |
|---|---|---|---|---|
| 1 | 99.4 | 0.5 | 0.1 | 0.6 ± 0.8 |
| 2 | 99.4 | 0.48 | 0.12 | 1.1 ± 1.7 |
| 3 | 99.4 | 0.34 | 0.15 | 0.5 ± 1.0 |
| 4 | 99.4 | 0.40 | 0.20 | 3.6 ± 2.4 |
| 5 | 99.4 | 0.3 | 0.3 | 5.9 ± 3.1 |
| 6 | 99.0 | 0.5 | 0.5 | 3.4 ± 3.1 |
| 7 | 99.7 | 0.1 | 0.2 | 1.9 ± 3.1 |

The data in TABLE XXIII show runs 1–3 and 7 were suitable for use as a provisional luting cement according to the present invention.

Example 10

Various adhesion reducing primers were applied to tooth structure prior to application of a commercial glass ionomer permanent luting cement, either 3M™ Vitremer™ Luting Cement System ("Vitremer") or Espe™ Ketac-Cem™ Radiopaque Polymaleinate Glass Ionomer Cement ("Ketac-Cem"). The permanent luting cements were mixed according to manufacturer's instructions and the BSA values for the cement of each run determined using the procedure set out above in the Bulk Shear Adhesion Test.

Set out below in TABLE XXIV are the adhesion reducing primer, the permanent luting cement and the BSA values for each run.

TABLE XXIV

| Run no. | Adhesion Reducing Primer | Permanent Luting Cement | BSA MPa SD |
|---|---|---|---|
| 1 | $ZrO_2$:$SiO_2$ Filler[1] | Vitremer | 0 |
| 2 | $TiO_2$[2] | Vitremer | 2.8 ± 1.3 |
| 3 | TEGDMA[3] | Vitremer | 3.6 ± 1.0 |
| 4 | $PEG_{200}$[4] | Vitremer | 4.3 ± 1.6 |
| 5 | $PEG_{400}$ DMA | Vitremer | 4.4 ± 2.0 |
| 6 | $NaH_2PO_4.2H_2O$[5] | Vitremer | 0.5 ± 0.7 |
| 7 | Glycerol | Vitremer | 2.6 ± 1.3 |
| 8 | $NaH_2PO_4.2H_2O$ | Ketac-Cem | 1.7 ± 1.7 |
| 9 | $ZrO_2$:$SiO_2$ Filler | Ketac-Cem | 1.6 ± 0.4 |

[1] A slurry of 2.0 g zirconia:silica filler of PREPARATORY EXAMPLE 3, but not silane treated, 0.7 g $K_3PO_4.7H_2O$ (60 weight % in water) and 0.9 g water.
[2] A slurry of 2.4 g $TiO_2$, 1.3 g $K_3PO_4.7H_2O$ (50 weight % in water) and 1.1 g deionized water.
[3] Rohm Tech, Inc., Malden, MA.
[4] Carbowax ™, Union Carbide.
[5] 57 Weight % in water.

For run no. 1, the PCC was evaluated using the procedure of EXAMPLE 1 and was 5.8±2.6.

The data in TABLE XXIV show runs 1, 6, 8, and 9 were suitable for use as provisional luting cements according to the present invention.

Example 11

The properties of a number of commercial provisional luting cements were compared to the properties of both a glass ionomer permanent luting cement, 3M™ Vitremer™ Luting Cement System, and one of the glass ionomer provisional luting cements of the invention. Set out in TABLE XXV are the luting cement, the BSA, CS, DTS, PCC, fluoride release at 14 days and AV. Each commercial cement was mixed according to the manufacturer's instructions.

TABLE XXV

| Luting Cement | BSA MPa SD | CS (MPa) | DTS (MPa) | PCC (MPa) | F Release (µg/g) | AV (MPa) |
|---|---|---|---|---|---|---|
| Temp Bond[1] | 0.0 ± 0.0 | 12.4 | | 4.3 ± 1.8 | 0 | 0.1 ± 0.2 |
| | | | | 1.7 ± 1.5 | | 0.0 ± 0.1 |
| Temp Bond NE[2] | 0.0 ± 0.0 | 8.3 | 2.1 | | | |
| Neo Temp[3] | 0.0 ± 0.0 | 37.3 | 15.2 | | 0 | 6.5 ± 1.3 |
| | | | | | | 5.9 ± 3.8 |
| ZOE 2200[4] | | 33.8 | 4.8 | | | |
| EX 3, Run No. 23 | 0.1 ± 0.3 | 3.4 | | 1.6 ± 2.9 | 2400 | 2.0 ± 0.4 |
| Vitremer | 4.1 ± 2.1 | 128.6 | 23.5 | | 1300 | |

[1] Temp-Bond ™ Temporary Cement (Kerr Manufacturing Co. Romulus, MI).
[2] Temp-Bond ™ NE ™ Non-Eugenol Temporary Cement (Kerr).
[3] Neo-Temp ™ Resin Cement (Teledyne-Getz, Elk Grove Village, IL).
[4] Caulk ™ Dentsply ™ ZOE 200 ™ Temporary Cement (L.D. Caulk Division of Dentsply International Inc., Melford DE).

The data in TABLE XXV show that the provisional luting cement of the present invention has a BSA that is comparable to commercially available provisional luting cements, yet has substantial fluoride release.

Example 12

The ingredients set out below in TABLE XXVI were independently combined to form three Paste I compositions designated Paste Ia, Paste Ib and Paste Ic.

TABLE XXVI

| Paste I | H$_2$O[1] | CP[2] | PAA[3] | PEG400[4] | DMAPE[5] | Glass[6] | OX-50[7] |
|---|---|---|---|---|---|---|---|
| Ia | 14 | — | — | 21 | 0.0875 | 65 | — |
| Ib | 54.72 | 13.7 | — | — | 1.368 | — | 31.6 |
| Ic | — | — | 72 | — | 0.5 | — | 28 |

[1]Deionized water.
[2]Ethylenically unsaturated acidic copolymer prepared like the precipitated dry polymer of EXAMPLE 11 of U.S. Pat. No. 5,130,347.
[3]Polyacrylic acid (molecular weight 5000; 50% aqueous solution; Aldrich Chemical Company, Inc.).
[4]Polyethylene glycol (molecular weight 400; Carbowax ™, Union Carbide).
[5]Glass of PREP. EX. 1.
[6]Fumed silica of PREP. EX. 4.

The ingredients set out below in TABLE XXVII were independently combined to form four Paste II compositions designated Paste Ia, Paste IIb, Paste IIc and Paste IId.

TABLE XXVII

| Paste II | PEG400 | Glass | OX-50 | CP | HEMA | PEG$_{400}$DMA | BPO* | BHT |
|---|---|---|---|---|---|---|---|---|
| IIa | — | — | 40 | 9.3 | 20.7 | 30 | 0.48 | 0.048 |
| IIb | — | 50 | — | 15 | 35 | — | 0.4 | 0.04 |
| IIc | — | 45 | 25 | — | — | 30 | 0.3 | 0.024 |
| IId | 9 | 45 | 25 | — | — | 21 | 0.3 | 0.03 |

*Benzoyl peroxide.

Cement compositions were prepared by hand spatulating the Paste I:Paste II formulations set out below in TABLE XXVIII in a 1:1 ratio by volume. BSA, CS and DTS of each resultant cement were measured. BSA was measured as detailed in the Bulk Shear Adhesion Test except that instead of conditioning the freshly ground dentin substrates at 37° C./95% RH, the samples were blown dry with filtered air immediately prior to applying the cement composition. CS and DTS were determined using the procedure described in EXAMPLE 1. Gel time was measured as the time from the start of mix until some polymerization of the cement was observed.

TABLE XXVIII

| Run No. | Paste I: Paste II | BSA MPa SD | CS (MPa) | DTS (MPa) | Gel Time Min.:Sec. |
|---|---|---|---|---|---|
| 1 | Ia:IIa | 0.10 ± 0.12 | 21.4 | 4.3 | 3:45 |
| 2 | Ia:IIb | 0.19 ± 0.28 | 23.0 | 3.5 | 1:45 |
| 3 | Ib:IIa | 0 ± 0 | 29.6 | 6.5 | 1:45 |
| 4 | Ib:IIb | 1.28 ± 1.76 | 66.0 | 15.3 | 2:00 |
| 5 | Ic:IIc | 0 ± 0 | 71.1 | 14.1 | — |
| 6 | Ic:IId | 0 ± 0 | 22.4 | 4.6 | — |

The data in TABLE XXVIII show paste:paste glass ionomer compositions exhibiting low bulk shear adhesion required for a provisional luting cement as well as good CS and DTS properties. The gel times show adequate working time for a practitioner to use the cement.

What is claimed:

1. A method for luting a prosthetic device to tooth structure comprising the steps of
   (i) providing a kit containing components (A), (B), and (C), wherein said components comprise:
      (A) a composition comprising a water miscible, acidic polymer
      (B) a composition comprising a finely divided, acid-reactive filler and an adhesion reducing component such that when mixed with component (A), the Bulk Shear Adhesion of the resulting cement is less then 2.0 MPa
      (C) a composition comprising a finely divided, acid-reactive filler such that when mixed with component (A), the Bulk Shear Adhesion of the resulting cement is greater than 2.0 MPa
   (ii) determining whether a provisional luting cement is required or a permanent luting cement,
   (iii) if a provisional luting cement is required, mixing (A) with (B), and omitting step (iv),
   (iv) if a permanent luting cement is required, mixing (A) with (C),
   (v) applying the cement created by step (iii) or (iv) on the prosthetic device and/or the tooth structure, and
   (vi) bonding the device to tooth structure.

2. A method according to claim 1 wherein (A) is a liquid and (B) and (C) are powders.

3. A method according to claim 1 wherein (A), (B) and (C) are pastes.

4. A method according to claim 1 wherein (A) is a liquid and (B) and (C) are pastes.

5. A method according to claim 1 wherein (A), (B) and (C) are powders, further comprising (D) water.

6. A method according to claim 1, wherein said provisional luting cement has a Bulk Shear Adhesion less than 1.0 MPa.

7. A method according to claim 1, wherein said provisional luting cement has a Bulk Shear Adhesion less than 0.5 MPa.

8. A method according to claim 1, further comprising an adhesion reducing primer, said primer being applied to tooth structure prior to application of said provisional luting cement.

9. A method for luting a prosthetic device to tooth structure comprising the steps of:
   (i) providing a kit containing components (A), (B), and (C), wherein said components comprise:
      (A) a composition comprising a water miscible, acidic polymer and an adhesion reducing component such that when mixed with component (C) the Bulk Shear Adhesion of the resulting cement is less than 2.0 MPa
      (B) a composition comprising a water miscible, acidic polymer such that when mixed with component (C), the Bulk Shear Adhesion of the resulting cement is greater than 2.0 MPa
      (C) a composition comprising a finely divided, acid-reactive filler
   (ii) determining whether a provisional luting cement is required or a permanent luting cement,
   (iii) if a provisional luting cement is required, mixing (A) with (C), and omitting step (iv), (iv) if a permanent luting cement is required, mixing (B) with (C), (v) applying the cement created by step (iii) or (iv) on the prosthetic device and/or the tooth structure, and (vi) bonding the device to tooth structure.

10. A method according to claim 9, wherein said provisional luting cement has a Bulk Shear Adhesion less than 1.0 MPa.

11. A method according to claim 9, wherein said provisional luting cement has a Bulk Shear Adhesion less than 0.5 MPa.

12. A method according to claim 9, further comprising an adhesion reducing primer, said primer being applied to tooth structure prior to application of said provisional luting cement.

* * * * *

UNITED STATES PATENT AND TRADEMARK OFFICE
CERTIFICATE OF CORRECTION

PATENT NO.: 5,814,682

DATED: September 29, 1998

INVENTOR(S): Richard P. Rusin, Paula D. Ario, Dwight W. Jacobs, Joel D. Oxman, Sumita B. Mitra, Ronald M. Randklev It is certified that error appears in the above-identified patent and that said Letters Patent is hereby corrected as shown below:

Claim 1, Column 35, line 63, Insert --:-- following "steps of".

Signed and Sealed this

Twenty-ninth Day of May, 2001

*Attest:*

NICHOLAS P. GODICI

*Attesting Officer*     *Acting Director of the United States Patent and Trademark Office*